(12) United States Patent
Mizutani et al.

(10) Patent No.: US 12,270,060 B2
(45) Date of Patent: Apr. 8, 2025

(54) PRODUCTION METHOD FOR L-CYCLIC AMINO ACIDS

(71) Applicant: UBE Corporation, Yamaguchi (JP)

(72) Inventors: Masaharu Mizutani, Hyogo (JP); Ryoma Miyake, Tokyo (JP); Hiroshi Kawabata, Tokyo (JP)

(73) Assignee: UBE CORPORATION, Yamaguchi (JP)

( * ) Notice: Subject to any disclaimer, the term of this patent is extended or adjusted under 35 U.S.C. 154(b) by 591 days.

(21) Appl. No.: 17/606,123

(22) PCT Filed: May 15, 2020

(86) PCT No.: PCT/JP2020/019517
§ 371 (c)(1),
(2) Date: Oct. 25, 2021

(87) PCT Pub. No.: WO2020/218624
PCT Pub. Date: Oct. 29, 2020

(65) Prior Publication Data
US 2022/0275410 A1  Sep. 1, 2022

(30) Foreign Application Priority Data

Apr. 25, 2019  (JP) ................. 2019-084234

(51) Int. Cl.
| C12P 13/04 | (2006.01) |
| C12N 9/10 | (2006.01) |
| C12N 15/70 | (2006.01) |
| C12P 41/00 | (2006.01) |

(52) U.S. Cl.
CPC ............ *C12P 13/04* (2013.01); *C12N 9/1096* (2013.01); *C12N 15/70* (2013.01); *C12P 41/006* (2013.01)

(58) Field of Classification Search
CPC .......... C12P 13/24; C12P 17/12; C12N 15/70
See application file for complete search history.

(56) References Cited

U.S. PATENT DOCUMENTS

2005/0038255 A1  2/2005  Thibaut et al.

FOREIGN PATENT DOCUMENTS

| EP | 1033405 A2 | 9/2000 |
| EP | 2889378 A1 | 7/2015 |
| JP | 2005-095167 A | 4/2005 |
| JP | 4590981 B2 | 12/2010 |
| WO | 2002/101003 A2 | 12/2002 |
| WO | 2015/033636 A1 | 3/2015 |

OTHER PUBLICATIONS

Office Action with Search Report that issued in corresponding Chinese patent Application No. 202080031314.1 dated Jan. 29, 2024, along with English translation thereof.
NAD(P)-binding Rossmann-fold superfamily protein [*Arabidopsis thaliana*] (AT5G52810), mRNA, NCBI Reference Sequence: NP_200093.1; Feb. 14, 2029.
Protein SAR Deficient 4 [Morus notabilis] (LOC21397372), mRNA, NCBI Reference Sequence: XP_010105735.1; Feb. 26, 2018.
Extended European Search Report issued in corresponding European patent Application No. 20795814.1 dated May 2, 2023.
Database UniProt [Online] May 14, 2014, Anonymous: "RecName: Full=Delta(1)-pyrroline-2-carboxylate reductase {ECO:0000256|Google:ProtNLM};", PX093040564 retrieved from EBI accession No. Uniprot: W9SGT1 Database accession No. W9SGT1.
Muramatsu et al., "The putative malate/lactate dehydrogenase from *Pseudomonas putida* is an NADPH-dependent $\Delta^1$-piperideine-2-carboxylate/ $\Delta^1$-pyrroline-2-carboxylate reductase involved in the catabolism of D-lysine and D-proline", The Journal of Biological Chemistry, vol. 280, No. 7, 2005, pp. 5329-5335.
Office Action issued in corresponding Japanese Application No. 2019-084234, dated May 9, 2023, along with English thereof.
Hartmann et al., "L-lysine metabolism to N-hydroxypipecolic acid: an integral immune-activating pathway in plants", The Plant Journal, 2018, vol. 96, pp. 5-21.
Hartmann et al., "Biochemical Principles and Functional Aspects of Pipecolic Acid Biosynthesis in Plant Immunity", Plant Physiology, 2017, vol. 174, pp. 124-153.
Ding et al., "Characterization of a Pipecolic Acid Biosynthesis Pathway Required for Systemic Acquired Resistance", The Plant Cell, 2016, vol. 28, pp. 2603-2615.
Definition Predicted: Morus Notabilis Protein SAR Deficient 4 (LOC21397372), mRNA, Database GenBank [online] and Accession XM_010107433, 2018, [retrieved on Apr. 28, 2023]URL: https://www.ncbi.nlm.nih.gov/nuccore/1350290039?sat=4&satkey= 214434102.
NAD(P)-binding Rossmann-fold superfamily protein [*Arabidopsis thaliana*] (AT5G52810), mRNA, NCBI Reference Sequence: NP_200093.1; Feb. 14, 2019.
Fernández-García et al. Tetrahedron: Asymmetry, vol. 6, No. 12, 1995, pp. 2905-2906.
Fujii et al. Bioscience, Biotechnology, and Biochemistry, vol. 66 (9), 2002, pp. 1981-1984.
Costilow et al. The Journal of Biological Chemistry, vol. 246, No. 21, 1971, pp. 6655-6660.
Meister et al. Journal of Biological Chemistry, vol. 229, Issue 2, 1957, pp. 789-800.

(Continued)

*Primary Examiner* — Tekchand Saidha
(74) *Attorney, Agent, or Firm* — GREENBLUM & BERNSTEIN, P.L.C.

(57) ABSTRACT

An object of the present invention is to provide a method of industrially producing a high-purity L-cyclic amino acid more inexpensively and with a high efficiency, from a cyclic amino acid having a double bond at the 1-position. The present invention provides a method in which an L-cyclic amino acid is produced by allowing a cyclic amino acid having a double bond at the 1-position to react with a specific enzyme having a catalytic ability to reduce a cyclic amino acid having a double bond at the 1-position to produce an L-cyclic amino acid.

7 Claims, 3 Drawing Sheets

Specification includes a Sequence Listing.

(56) References Cited

OTHER PUBLICATIONS

Payton et al. Journal of Bacteriology, vol. 149, No. 3, 1982, pp. 864-871.
Database UniProtRB/TrEMBL [online], accession No. W9SGT1, <https://www.uniprot.org/uniprot/>, May 14, 2014 upload, He, N., Zhao, S., Definition: SubName: Full=Uncharacterized protein {ECO:0000313|EMBL:EXC05955.1}, cols. OS, SQ.
International Search Report for PCT/JP2020/019517, dated Jun. 30, 2020, along with an English translation thereof.
International Preliminary Report on Patentability issued in PCT/JP2020/019517, dated Sep. 28, 2021, along with an English translation thereof.

(1)

(2)

(3)

(1)

(2)

(3)

SEQUENCE LISTING

<160> NUMBER OF SEQ ID NOS: 21

<210> SEQ ID NO 1
<211> LENGTH: 978
<212> TYPE: DNA
<213> ORGANISM: Arabidopsis thaliana

<400> SEQUENCE: 1

```
atggctgcat taccagtatt cataccagca gagtcatttc catcgatcct ctcacatgaa      60
accttgatca atcactttcg gaccaatctt ccgaaacatt catcaacaat cacaagccct     120
gtccggcaaa actacaccgt ttcatcacct tcctctctcc tcctcatgcc ttcttggtca     180
tcttcttctt ctctccctta catgggcgtc aagctcgtga cctatttccc tcataactct     240
tctcagaact tacctggcat ccatggatcc tacacactct ttagctccac tacaggccaa     300
accttagcta caatggatgg tactgtttta accctttacc gtacttcctc tgtttcaggc     360
ttaggatcca aaatcctagc tagagacgat agtcaagtgc tgatcatggt tggttccggt     420
gctctcgcac cacacctgat caaatcccat ctagctgcga gaccaagctt gagaagagtg     480
atcatatgga acagaactcc acaagggct caggagttag ctgaaaccct ctccaaggat     540
cctcaacaca aggagatttc attcgatagc cacgattcgc tagatcaaat cattcctcta     600
ggagatatta taagctgtgc aacaaactca actgttccat tggtcaaagg tgagttcttg     660
aaacccggaa cccatcttga ccttgctgga tcgtttagcc atgaaatgaa ggaatgtgac     720
gacaatgcga tacagagagg gagtgtgttt gtcgataatg acactgcgat gatagaagca     780
ggagagctcg cgggagcgtt tgagagagga gtgattaaga gagaagacat ttgtgggaat     840
ttggtggagt tgatcaaagg tgacaaagaa gggagaaaga gttcaacaga cataacagtg     900
tttaagtccg tcggttcggg taccgtagat ctcttaaccg cacaacttgt tcacgagact     960
tacctcagcc gttgttaa                                                   978
```

<210> SEQ ID NO 2
<211> LENGTH: 325
<212> TYPE: PRT
<213> ORGANISM: Arabidopsis thaliana

<400> SEQUENCE: 2

Met Ala Ala Leu Pro Val Phe Ile Pro Ala Glu Ser Phe Pro Ser Ile

```
              1               5                  10                 15
            Leu Ser His Glu Thr Leu Ile Asn His Phe Arg Thr Asn Leu Pro Lys
                            20                  25                 30

His Ser Ser Thr Ile Thr Ser Pro Val Arg Gln Asn Tyr Thr Val Ser
                            35                  40                 45

Ser Pro Ser Ser Leu Leu Met Pro Ser Trp Ser Ser Ser Ser
                50                  55                  60

Leu Pro Tyr Met Gly Val Lys Leu Val Thr Tyr Phe Pro His Asn Ser
            65                  70                  75                 80

Ser Gln Asn Leu Pro Gly Ile His Gly Ser Tyr Thr Leu Phe Ser Ser
                            85                  90                 95

Thr Thr Gly Gln Thr Leu Ala Thr Met Asp Gly Thr Val Leu Thr Leu
                            100                 105                110

Tyr Arg Thr Ser Ser Val Ser Gly Leu Gly Ser Lys Ile Leu Ala Arg
                            115                 120                125

Asp Asp Ser Gln Val Leu Ile Met Val Gly Ser Gly Ala Leu Ala Pro
                            130                 135                140

His Leu Ile Lys Ser His Leu Ala Ala Arg Pro Ser Leu Arg Arg Val
            145                 150                 155                160

Ile Ile Trp Asn Arg Thr Pro Gln Arg Ala Gln Glu Leu Ala Glu Thr
                            165                 170                175

Leu Ser Lys Asp Pro Gln His Lys Glu Ile Ser Phe Asp Ser His Asp
                            180                 185                190

Ser Leu Asp Gln Ile Ile Pro Leu Gly Asp Ile Ile Ser Cys Ala Thr
                            195                 200                205

Asn Ser Thr Val Pro Leu Val Lys Gly Glu Phe Leu Lys Pro Gly Thr
                            210                 215                220

His Leu Asp Leu Ala Gly Ser Phe Ser His Glu Met Lys Glu Cys Asp
            225                 230                 235                240

Asp Asn Ala Ile Gln Arg Gly Ser Val Phe Val Asp Asn Asp Thr Ala
                            245                 250                255

Met Ile Glu Ala Gly Glu Leu Ala Gly Ala Phe Glu Arg Gly Val Ile
                            260                 265                270

Lys Arg Glu Asp Ile Cys Gly Asn Leu Val Glu Leu Ile Lys Gly Asp
                            275                 280                285

Lys Glu Gly Arg Lys Ser Ser Thr Asp Ile Thr Val Phe Lys Ser Val
                            290                 295                300

Gly Ser Gly Thr Val Asp Leu Leu Thr Ala Gln Leu Val His Glu Thr
            305                 310                 315                320

Tyr Leu Ser Arg Cys
                            325

<210> SEQ ID NO 3
<211> LENGTH: 999
<212> TYPE: DNA
<213> ORGANISM: Morus alba

<400> SEQUENCE: 3
atggcttcca caaccaccgc cataacatcc ccaatcttca tcaccactca atcctttcac      60
accatcctct ctcgccaaac tcttatggac cacttccatt cgtctctccc cacagtctct     120
gcttctctct ctaccccact ccgccaaaac cacgccgttt cacccacctc ctctctcctc     180
ctcatgccct tggtccac ctctccttct tcccttaca ttggcgtcaa gctagtcact       240
tacttccctc aaagctccac cttaagttta cccggcattc acgccagtta cgtcctcttc     300
```

```
agctccgcaa ctgggcagac cttggcttcc atggacggaa ctgcactgac cctttcaga      360 acttcatgtg tttctggctt ggcttcccgg attttggcca gagacgacag caaagtcctc      420
gtcatgatcg gtgcgggcgc cttggcgccg catttgatca aggcccatct caccgcgaga      480
cccggtttgg agagagttgt catctggaac cgcacggtgg agaaagctag aaacttggct      540
gagcaactgc aacaaagttc ggggcttgac ggggtttgtt tcgagagtaa tgggtgcttg      600
gaggaagttg ttgggatggg agatattgtg agctgcgcaa cgaactcgga ggcgcctctt      660
gtgaagggcc agaagctgaa gccaggggca catcttgact tggttgggtc attcaagcac      720
tcaatgaggg agtgtgatga cgaggcgatt cagagaggta gaattttgt ggacaatgag       780 gctgcgttgg tggaggcagg agagttggtg ggcgcttttg agagaggtgt gattacgaaa      840
gaagacattg gagggaattt ggtggaactt ataatggggg agaaggttgg aagaagagat      900
tctgaggagg tcactgtgtt taagtccgtt ggatccgcag cggtggatat tcttgctgca      960
caattggtgt atgagaccta tttgcagcaa aataactag                              999
```

<210> SEQ ID NO 4
<211> LENGTH: 332
<212> TYPE: PRT
<213> ORGANISM: Morus alba

<400> SEQUENCE: 4

```
Met Ala Ser Thr Thr Thr Ala Ile Thr Ser Pro Ile Phe Ile Thr Thr
  1               5                  10                  15

Gln Ser Phe His Thr Ile Leu Ser Arg Gln Thr Leu Met Asp His Phe
             20                  25                  30

His Ser Ser Leu Pro Thr Val Ser Ala Ser Leu Ser Thr Pro Leu Arg
         35                  40                  45

Gln Asn His Ala Val Ser Pro Thr Ser Ser Leu Leu Leu Met Pro Ser
     50                  55                  60

Trp Ser Thr Ser Pro Ser Leu Pro Tyr Ile Gly Val Lys Leu Val Thr
 65                  70                  75                  80

Tyr Phe Pro Gln Ser Ser Thr Leu Ser Leu Pro Gly Ile His Ala Ser
                 85                  90                  95

Tyr Val Leu Phe Ser Ser Ala Thr Gly Gln Thr Leu Ala Ser Met Asp
            100                 105                 110

Gly Thr Ala Leu Thr Leu Phe Arg Thr Ser Cys Val Ser Gly Leu Ala
        115                 120                 125

Ser Arg Ile Leu Ala Arg Asp Asp Ser Lys Val Leu Val Met Ile Gly
    130                 135                 140

Ala Gly Ala Leu Ala Pro His Leu Ile Lys Ala His Leu Thr Ala Arg
145                 150                 155                 160

Pro Gly Leu Glu Arg Val Val Ile Trp Asn Arg Thr Val Glu Lys Ala
                165                 170                 175

Arg Asn Leu Ala Glu Gln Leu Gln Gln Ser Ser Gly Leu Asp Gly Val
            180                 185                 190

Cys Phe Glu Ser Asn Gly Cys Leu Glu Glu Val Val Gly Met Gly Asp
        195                 200                 205

Ile Val Ser Cys Ala Thr Asn Ser Glu Ala Pro Leu Val Lys Gly Gln
    210                 215                 220

Lys Leu Lys Pro Gly Ala His Leu Asp Leu Val Gly Ser Phe Lys His
225                 230                 235                 240

Ser Met Arg Glu Cys Asp Asp Glu Ala Ile Gln Arg Gly Arg Ile Phe
```

```
                    245                 250                 255
Val Asp Asn Glu Ala Ala Leu Val Glu Ala Gly Glu Leu Val Gly Ala
            260                 265                 270

Phe Glu Arg Gly Val Ile Thr Lys Glu Asp Ile Gly Gly Asn Leu Val
        275                 280                 285

Glu Leu Ile Met Gly Glu Lys Val Gly Arg Arg Asp Ser Glu Val
        290                 295                 300

Thr Val Phe Lys Ser Val Gly Ser Ala Ala Val Asp Ile Leu Ala Ala
305                 310                 315                 320

Gln Leu Val Tyr Glu Thr Tyr Leu Gln Gln Asn Asn
                325                 330

<210> SEQ ID NO 5
<211> LENGTH: 1035
<212> TYPE: DNA
<213> ORGANISM: Lathyrus japonicus

<400> SEQUENCE: 5
atggcttccg caaacaaaga ccaaaaaacc acaaacaccg tgtcgtcttc ttcttcttct      60
tcttctccaa tcttcatttc cactgagaat ttacaaacta tcctcaccca tcaaactcta     120
atgaagcaca tcgactccaa tctccccaaa gtttcaacct ttctccaaac cccaattcgc     180
caacactata gtctctctcc ttcctcttct ctcctcctca tgccttcatg gtcttcttct     240
tcctccttcc cttacgttgg tgtcaaactt gtgacccatt tccctcaaaa ttcctcaatc     300
aatttacctg tgttcaagg tagctatgtc ctcttcaatt caaccacggg tcaaaccctt     360
gcttctatgg attccacgga acttacgctt tacagaacct cttgtgtctc tggtttggct     420
tctagatatt tatctagaga tgatagtgag gttcttgtta tggttggtgc tggtccccct     480
gcacctcatt tgatcagagc tcattttca gctagaccca gtttgagaaa agtgttgatt     540
tggaatagga ctgttgaaaa ggcagaagct ttggctaaga atctgagaga aagtgatgag     600
ttttcactct cagggttgag ttttgagggt tgtgggtgtt tgaatgaggt tgttggactt     660
ggggatattg tgagctgtgc tacaaattcc gagatggcgc ttgtgaaagg tgagaggttg     720
aaggttggag ctcatttgga tttggtgggt tcttttaagc cttcaatgaa ggaatgtgat     780
gatgaggctt tgaaaagggg gaaagtgttt gtggacaatg aggctgcatt ggttgaagca     840
ggggagctgg tgggtgcttt tgaaagggga gtgatcaagg aagatgaaat tgaggcaaat     900
ttggtggagc ttattagagg tgataaagtt gggagaagaa gttcagagga aattactgtt     960
tttaagtctg ttggttctgc tgttgttgat atgctggctg cacagtttgt ttatgagtca    1020
tacataggaa aatag                                                    1035

<210> SEQ ID NO 6
<211> LENGTH: 344
<212> TYPE: PRT
<213> ORGANISM: Lathyrus japonicus

<400> SEQUENCE: 6

Met Ala Ser Ala Asn Lys Asp Gln Lys Thr Thr Asn Thr Val Ser Ser
1               5                   10                  15

Ser Ser Ser Ser Ser Pro Ile Phe Ile Ser Thr Glu Asn Leu Gln
            20                  25                  30

Thr Ile Leu Thr His Gln Thr Leu Met Lys His Ile Asp Ser Asn Leu
        35                  40                  45

Pro Lys Val Ser Thr Phe Leu Gln Thr Pro Ile Arg Gln His Tyr Ser
```

|     |     |     |     |     | 50  |     |     |     | 55  |     |     |     |     | 60  |     |     |     |     |
| --- | --- | --- | --- | --- | --- | --- | --- | --- | --- | --- | --- | --- | --- | --- | --- | --- | --- | --- |

Leu Ser Pro Ser Ser Leu Leu Met Pro Ser Trp Ser Ser
65                  70                  75                  80

Ser Ser Phe Pro Tyr Val Gly Val Lys Leu Val Thr His Phe Pro Gln
                85                  90                  95

Asn Ser Ser Ile Asn Leu Pro Gly Val Gln Gly Ser Tyr Val Leu Phe
            100                 105                 110

Asn Ser Thr Thr Gly Gln Thr Leu Ala Ser Met Asp Ser Thr Glu Leu
        115                 120                 125

Thr Leu Tyr Arg Thr Ser Cys Val Ser Gly Leu Ala Ser Arg Tyr Leu
    130                 135                 140

Ser Arg Asp Asp Ser Glu Val Leu Val Met Val Gly Ala Gly Pro Leu
145                 150                 155                 160

Ala Pro His Leu Ile Arg Ala His Phe Ser Ala Arg Pro Ser Leu Arg
                165                 170                 175

Lys Val Leu Ile Trp Asn Arg Thr Val Glu Lys Ala Glu Ala Leu Ala
            180                 185                 190

Lys Asn Leu Arg Glu Ser Asp Glu Phe Ser Leu Ser Gly Leu Ser Phe
        195                 200                 205

Glu Gly Cys Gly Cys Leu Asn Glu Val Val Gly Leu Gly Asp Ile Val
    210                 215                 220

Ser Cys Ala Thr Asn Ser Glu Met Ala Leu Val Lys Gly Glu Arg Leu
225                 230                 235                 240

Lys Val Gly Ala His Leu Asp Leu Val Gly Ser Phe Lys Pro Ser Met
                245                 250                 255

Lys Glu Cys Asp Asp Glu Ala Leu Lys Arg Gly Lys Val Phe Val Asp
            260                 265                 270

Asn Glu Ala Ala Leu Val Glu Ala Gly Glu Leu Val Gly Ala Phe Glu
        275                 280                 285

Arg Gly Val Ile Lys Glu Asp Glu Ile Glu Ala Asn Leu Val Glu Leu
    290                 295                 300

Ile Arg Gly Asp Lys Val Gly Arg Arg Ser Ser Glu Glu Ile Thr Val
305                 310                 315                 320

Phe Lys Ser Val Gly Ser Ala Val Val Asp Met Leu Ala Ala Gln Phe
                325                 330                 335

Val Tyr Glu Ser Tyr Ile Gly Lys
            340

<210> SEQ ID NO 7
<211> LENGTH: 1665
<212> TYPE: DNA
<213> ORGANISM: Artificial Sequence
<220> FEATURE:
<223> OTHER INFORMATION: fusion protein

<400> SEQUENCE: 7
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300 gatattgat acggtgtttc gagaattgca tatagtaaag actttgaaac tctcaaagtt     360
gattttctta gcaagctacc tgaaatgctg aaaatgttcg aagatcgttt atgtcataaa     420

```
acatatttaa atggtgatca tgtaacccat cctgacttca tgttgtatga cgctcttgat    480
gttgttttat acatggaccc aatgtgcctg atgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatcccc ggaattcatg gctgcattac cagtattcat accagcagag    720
tcatttccat cgatcctctc acatgaaacc ttgatcaatc actttcggac caatcttccg    780
aaacattcat caacaatcac aagccctgtc cggcaaaact acaccgtttc atcaccttcc    840
tctctcctcc tcatgccttc ttggtcatct tcttcttctc tcccttacat gggcgtcaag    900
ctcgtgacct atttccctca taactcttct cagaacttac ctggcatcca tggatcctac    960
acactcttta gctccactac aggccaaacc ttagctacaa tggatggtac tgttttaacc    1020
ctttaccgta cttcctctgt ttcaggctta ggatccaaaa tcctagctag agacgatagt    1080
caagtgctga tcatggttgg ttccggtgct ctcgcaccac acctgatcaa atcccatcta    1140
gctgcgagac caagcttgag aagagtgatc atatggaaca gaactccaca agggctcag    1200 gagttagctg aaaccctctc caaggatcct caacacaagg agatttcatt cgatagccac    1260
gattcgctag atcaaatcat tcctctagga gatattataa gctgtgcaac aaactcaact    1320
gttccattgg tcaaaggtga gttcttgaaa cccggaaccc atcttgacct tgctggatcg    1380
tttagccatg aaatgaagga atgtgacgac aatgcgatac agagagggag tgtgtttgtc    1440
gataatgaca ctgcgatgat agaagcagga gagctcgcgg gagcgtttga gagaggagtg    1500
attaagagag aagacatttg tgggaatttg gtggagttga tcaaggtgga caaagaaggg    1560
agaaagagtt caacagacat aacagtgttt aagtccgtcg gttcgggtac cgtagatctc    1620
ttaaccgcac aacttgttca cgagacttac ctcagccgtt gttaa               1665
```

<210> SEQ ID NO 8
<211> LENGTH: 554
<212> TYPE: PRT
<213> ORGANISM: Artificial Sequence
<220> FEATURE:
<223> OTHER INFORMATION: fusion protein

<400> SEQUENCE: 8

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
            165                 170                 175

Val Cys Phe Lys Lys Arg Ile Glu Ala Ile Pro Gln Ile Asp Lys Tyr
        180                 185                 190

Leu Lys Ser Ser Lys Tyr Ile Ala Trp Pro Leu Gln Gly Trp Gln Ala
    195                 200                 205

Thr Phe Gly Gly Gly Asp His Pro Pro Lys Ser Asp Leu Val Pro Arg
210                 215                 220

Gly Ser Pro Glu Phe Met Ala Ala Leu Pro Val Phe Ile Pro Ala Glu
225                 230                 235                 240

Ser Phe Pro Ser Ile Leu Ser His Glu Thr Leu Ile Asn His Phe Arg
                245                 250                 255

Thr Asn Leu Pro Lys His Ser Ser Thr Ile Thr Ser Pro Val Arg Gln
            260                 265                 270

Asn Tyr Thr Val Ser Ser Pro Ser Ser Leu Leu Met Pro Ser Trp
        275                 280                 285

Ser Ser Ser Ser Ser Leu Pro Tyr Met Gly Val Lys Leu Val Thr Tyr
290                 295                 300

Phe Pro His Asn Ser Ser Gln Asn Leu Pro Gly Ile His Gly Ser Tyr
305                 310                 315                 320

Thr Leu Phe Ser Ser Thr Thr Gly Gln Thr Leu Ala Thr Met Asp Gly
                325                 330                 335

Thr Val Leu Thr Leu Tyr Arg Thr Ser Ser Val Ser Gly Leu Gly Ser
            340                 345                 350

Lys Ile Leu Ala Arg Asp Asp Ser Gln Val Leu Ile Met Val Gly Ser
        355                 360                 365

Gly Ala Leu Ala Pro His Leu Ile Lys Ser His Leu Ala Ala Arg Pro
370                 375                 380

Ser Leu Arg Arg Val Ile Ile Trp Asn Arg Thr Pro Gln Arg Ala Gln
385                 390                 395                 400

Glu Leu Ala Glu Thr Leu Ser Lys Asp Pro Gln His Lys Glu Ile Ser
                405                 410                 415

Phe Asp Ser His Asp Ser Leu Asp Gln Ile Ile Pro Leu Gly Asp Ile
            420                 425                 430

Ile Ser Cys Ala Thr Asn Ser Thr Val Pro Leu Val Lys Gly Glu Phe
        435                 440                 445

Leu Lys Pro Gly Thr His Leu Asp Leu Ala Gly Ser Phe Ser His Glu
    450                 455                 460

Met Lys Glu Cys Asp Asp Asn Ala Ile Gln Arg Gly Ser Val Phe Val
465                 470                 475                 480

Asp Asn Asp Thr Ala Met Ile Glu Ala Gly Glu Leu Ala Gly Ala Phe
                485                 490                 495

Glu Arg Gly Val Ile Lys Arg Glu Asp Ile Cys Gly Asn Leu Val Glu
            500                 505                 510

Leu Ile Lys Gly Asp Lys Glu Gly Arg Lys Ser Ser Thr Asp Ile Thr
        515                 520                 525

Val Phe Lys Ser Val Gly Ser Gly Thr Val Asp Leu Leu Thr Ala Gln
    530                 535                 540

Leu Val His Glu Thr Tyr Leu Ser Arg Cys
545                 550
```

<210> SEQ ID NO 9
<211> LENGTH: 1677
<212> TYPE: DNA
<213> ORGANISM: Artificial Sequence
<220> FEATURE:
<223> OTHER INFORMATION: fusion protein

<400> SEQUENCE: 9

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ctggttccgc gtggatccat ggcttccaca accaccgcca acatccccc aatcttcatc    720
accactcaat cctttcacac catcctctct cgccaaactc ttatggacca cttccattcg    780
tctctcccca cagtctctgc ttctctctct accccactcc gccaaaacca cgccgtttca    840
cccacctcct ctctcctcct catgccctct ggtccacct ctccttctct cccttacatt    900
ggcgtcaagc tagtcactta cttccctcaa agctccacct taagtttacc cggcattcac    960
gccagttacg tcctcttcag ctccgcaact gggcagacct tggcttccat ggacggaact   1020
gcactgaccc ttttcagaac ttcatgtgtt tctggcttgg cttcccggat tttggccaga   1080
gacgacagca aagtcctcgt catgatcggt gcgggcgcct tggcgccgca tttgatcaag   1140
gcccatctca ccgcgagacc cggttttgga gagttgtca tctggaaccg cacggtggag   1200
aaagctagaa acttggctga gcaactgcaa caaagttcgg ggcttgacgg ggtttgtttc   1260
gagagtaatg ggtgcttgga ggaagttgtt gggatgggag atattgtgag ctgcgcaacg   1320
aactcggagg cgcctcttgt gaagggccag aagctgaagc caggggcaca tcttgacttg   1380
gttgggtcat tcaagcactc aatgaggag tgtgatgacg aggcgattca gagaggtaga   1440
atttttgtgg acaatgaggc tgcgttggtg gaggcaggag agttggtggg cgcttttgag   1500
agaggtgtga ttacgaaaga agacattgga gggaatttgg tggaacttat aatgggggag   1560
aaggttggaa gaagagattc tgaggaggtc actgtgttta gtccgttgg atccgcagcg   1620
gtggatattc ttgctgcaca attggtgtat gagacctatt gcagcaaaa taactag       1677
```

<210> SEQ ID NO 10
<211> LENGTH: 558
<212> TYPE: PRT
<213> ORGANISM: Artificial Sequence
<220> FEATURE:
<223> OTHER INFORMATION: fusion protein

<400> SEQUENCE: 10

Met Ser Pro Ile Leu Gly Tyr Trp Lys Ile Lys Gly Leu Val Gln Pro
1               5                   10                  15

-continued

Thr Arg Leu Leu Leu Glu Tyr Leu Glu Lys Tyr Glu His Leu
          20              25              30

Tyr Glu Arg Asp Glu Gly Asp Lys Trp Arg Asn Lys Lys Phe Glu Leu
        35              40              45

Gly Leu Glu Phe Pro Asn Leu Pro Tyr Ile Asp Gly Asp Val Lys
50                  55                  60

Leu Thr Gln Ser Met Ala Ile Ile Arg Tyr Ile Ala Asp Lys His Asn
65              70              75              80

Met Leu Gly Gly Cys Pro Lys Glu Arg Ala Glu Ile Ser Met Leu Glu
                85              90              95

Gly Ala Val Leu Asp Ile Arg Tyr Gly Val Ser Arg Ile Ala Tyr Ser
            100             105             110

Lys Asp Phe Glu Thr Leu Lys Val Asp Phe Leu Ser Lys Leu Pro Glu
        115             120             125

Met Leu Lys Met Phe Glu Asp Arg Leu Cys His Lys Thr Tyr Leu Asn
130             135             140

Gly Asp His Val Thr His Pro Asp Phe Met Leu Tyr Asp Ala Leu Asp
145             150             155             160

Val Val Leu Tyr Met Asp Pro Met Cys Leu Asp Ala Phe Pro Lys Leu
                165             170             175

Val Cys Phe Lys Lys Arg Ile Glu Ala Ile Pro Gln Ile Asp Lys Tyr
            180             185             190

Leu Lys Ser Ser Lys Tyr Ile Ala Trp Pro Leu Gln Gly Trp Gln Ala
        195             200             205

Thr Phe Gly Gly Gly Asp His Pro Pro Lys Ser Asp Leu Val Pro Arg
210             215             220

Gly Ser Met Ala Ser Thr Thr Ala Ile Thr Ser Pro Ile Phe Ile
225             230             235             240

Thr Thr Gln Ser Phe His Thr Ile Leu Ser Arg Gln Thr Leu Met Asp
                245             250             255

His Phe His Ser Ser Leu Pro Thr Val Ser Ala Ser Leu Ser Thr Pro
            260             265             270

Leu Arg Gln Asn His Ala Val Ser Pro Thr Ser Ser Leu Leu Leu Met
        275             280             285

Pro Ser Trp Ser Thr Ser Pro Ser Leu Pro Tyr Ile Gly Val Lys Leu
290             295             300

Val Thr Tyr Phe Pro Gln Ser Ser Thr Leu Ser Leu Pro Gly Ile His
305             310             315             320

Ala Ser Tyr Val Leu Phe Ser Ser Ala Thr Gly Gln Thr Leu Ala Ser
                325             330             335

Met Asp Gly Thr Ala Leu Thr Leu Phe Arg Thr Ser Cys Val Ser Gly
            340             345             350

Leu Ala Ser Arg Ile Leu Ala Arg Asp Asp Ser Lys Val Leu Val Met
        355             360             365

Ile Gly Ala Gly Ala Leu Ala Pro His Leu Ile Lys Ala His Leu Thr
370             375             380

Ala Arg Pro Gly Leu Glu Arg Val Val Ile Trp Asn Arg Thr Val Glu
385             390             395             400

Lys Ala Arg Asn Leu Ala Glu Gln Leu Gln Gln Ser Ser Gly Leu Asp
                405             410             415

Gly Val Cys Phe Glu Ser Asn Gly Cys Leu Glu Glu Val Val Gly Met
            420             425             430

Gly Asp Ile Val Ser Cys Ala Thr Asn Ser Glu Ala Pro Leu Val Lys

```
                        435                 440                 445
Gly Gln Lys Leu Lys Pro Gly Ala His Leu Asp Leu Val Gly Ser Phe
450                 455                 460

Lys His Ser Met Arg Glu Cys Asp Glu Ala Ile Gln Arg Gly Arg
465                 470                 475                 480

Ile Phe Val Asp Asn Glu Ala Ala Leu Val Glu Ala Gly Glu Leu Val
                485                 490                 495

Gly Ala Phe Glu Arg Gly Val Ile Thr Lys Glu Asp Ile Gly Gly Asn
                500                 505                 510

Leu Val Glu Leu Ile Met Gly Glu Lys Val Gly Arg Arg Asp Ser Glu
                515                 520                 525

Glu Val Thr Val Phe Lys Ser Val Gly Ser Ala Ala Val Asp Ile Leu
                530                 535                 540

Ala Ala Gln Leu Val Tyr Glu Thr Tyr Leu Gln Gln Asn Asn
545                 550                 555
```

<210> SEQ ID NO 11
<211> LENGTH: 1713
<212> TYPE: DNA
<213> ORGANISM: Artificial Sequence
<220> FEATURE:
<223> OTHER INFORMATION: fusion protein

<400> SEQUENCE: 11

| | |
|---|---|
| atgtccccta tactaggtta ttggaaaatt aagggccttg tgcaacccac tcgacttctt | 60 |
| ttggaatatc ttgaagaaaa atatgaagag catttgtatg agcgcgatga aggtgataaa | 120 |
| tggcgaaaca aaaagtttga attgggtttg gagtttccca atcttcctta ttatattgat | 180 |
| ggtgatgtta aattaacaca gtctatggcc atcatacgtt atagagctga caagcacaac | 240 |
| atgttgggtg gttgtccaaa agagcgtgca gagatttcaa tgcttgaagg agcggttttg | 300 |
| gatattagat acggtgtttc gagaattgca tatagtaaag actttgaaac tctcaaagtt | 360 |
| gattttctta gcaagctacc tgaaatgctg aaaatgttcg aagatcgttt atgtcataaa | 420 |
| acatatttaa atggtgatca tgtaacccat cctgacttca tgttgtatga cgctcttgat | 480 |
| gttgttttat acatggaccc aatgtgcctg gatgcgttcc caaaattagt ttgttttaaa | 540 |
| aaacgtattg aagctatccc acaaattgat aagtacttga atccagcaa gtatatagca | 600 |
| tggccttttgc agggctggca agccacgttt ggtggtggcg accatcctcc aaaatcggat | 660 |
| ctggttccgc gtggatccat ggcttccgca acaagacc aaaaaaccac aaacaccgtg | 720 |
| tcgtcttctt cttcttcttc ttctccaatc ttcatttcca ctgagaattt acaaactatc | 780 |
| ctcacccatc aaactctaat gaagcacatc gactccaatc tccccaaagt ttcaaccttt | 840 |
| ctccaaaccc caattcgcca acactatagt ctctctcctt cctcttctct cctcctcatg | 900 |
| ccttcatggt cttcttcttc ctccttccct tacgttggtg tcaaacttgt gacccatttc | 960 |
| cctcaaaatt cctcaatcaa tttacctggt gttcaaggta gctatgtcct cttcaattca | 1020 |
| accacgggtc aaacccttgc ttctatggat tccacggaac ttacgcttta cagaacctct | 1080 |
| tgtgtctctg gtttggcttc tagatattta tctagagatg atagtgaggt tcttgttatg | 1140 |
| gttggtgctg tccccttgc acctcatttg atcagagctc attttttcagc tagacccagt | 1200 |
| ttgagaaaag tgttgatttg aataggact gttgaaaagg cagaagcttt ggctaagaat | 1260 |
| ctgagagaaa gtgatgagtt ttcactctca gggttgagtt tgagggttg tgggtgtttg | 1320 |
| aatgaggttg ttggacttgg ggatattgtg agctgtgcta caaattccga gatggcgctt | 1380 |

```
gtgaaaggtg agaggttgaa ggttggagct catttggatt tggtgggttc ttttaagcct    1440
tcaatgaagg aatgtgatga tgaggctttg aaaaggggga agtgtttgt ggacaatgag     1500 gctgcattgg ttgaagcagg ggagctggtg ggtgcttttg aaaggggagt gatcaaggaa   1560
gatgaaattg aggcaaattt ggtggagctt attagaggtg ataaagttgg gagaagaagt   1620
tcagaggaaa ttactgtttt taagtctgtt ggttctgctg ttgttgatat gctggctgca   1680
cagtttgttt atgagtcata cataggaaaa tag                                 1713
```

```
<210> SEQ ID NO 12
<211> LENGTH: 570
<212> TYPE: PRT
<213> ORGANISM: Artificial Sequence
<220> FEATURE:
<223> OTHER INFORMATION: fusion protein

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Met Ala Ser Ala Asn Lys Asp Gln Lys Thr Thr Asn Thr Val
225                 230                 235                 240

Ser Ser Ser Ser Ser Ser Ser Pro Ile Phe Ile Ser Thr Glu Asn
                245                 250                 255

Leu Gln Thr Ile Leu Thr His Gln Thr Leu Met Lys His Ile Asp Ser
            260                 265                 270

Asn Leu Pro Lys Val Ser Thr Phe Leu Gln Thr Pro Ile Arg Gln His
        275                 280                 285

Tyr Ser Leu Ser Pro Ser Ser Leu Leu Leu Met Pro Ser Trp Ser
    290                 295                 300
```

```
Ser Ser Ser Ser Phe Pro Tyr Val Gly Val Lys Leu Val Thr His Phe
305                 310                 315                 320

Pro Gln Asn Ser Ser Ile Asn Leu Pro Gly Val Gln Gly Ser Tyr Val
            325                 330                 335

Leu Phe Asn Ser Thr Thr Gly Gln Thr Leu Ala Ser Met Asp Ser Thr
        340                 345                 350

Glu Leu Thr Leu Tyr Arg Thr Ser Cys Val Ser Gly Leu Ala Ser Arg
    355                 360                 365

Tyr Leu Ser Arg Asp Asp Ser Glu Val Leu Val Met Val Gly Ala Gly
370                 375                 380

Pro Leu Ala Pro His Leu Ile Arg Ala His Phe Ser Ala Arg Pro Ser
385                 390                 395                 400

Leu Arg Lys Val Leu Ile Trp Asn Arg Thr Val Glu Lys Ala Glu Ala
                405                 410                 415

Leu Ala Lys Asn Leu Arg Glu Ser Asp Glu Phe Ser Leu Ser Gly Leu
            420                 425                 430

Ser Phe Glu Gly Cys Gly Cys Leu Asn Glu Val Val Gly Leu Gly Asp
        435                 440                 445

Ile Val Ser Cys Ala Thr Asn Ser Glu Met Ala Leu Val Lys Gly Glu
450                 455                 460

Arg Leu Lys Val Gly Ala His Leu Asp Leu Val Gly Ser Phe Lys Pro
465                 470                 475                 480

Ser Met Lys Glu Cys Asp Asp Glu Ala Leu Lys Arg Gly Lys Val Phe
                485                 490                 495

Val Asp Asn Glu Ala Ala Leu Val Glu Ala Gly Glu Leu Val Gly Ala
            500                 505                 510

Phe Glu Arg Gly Val Ile Lys Glu Asp Glu Ile Glu Ala Asn Leu Val
        515                 520                 525

Glu Leu Ile Arg Gly Asp Lys Val Gly Arg Arg Ser Ser Glu Glu Ile
530                 535                 540

Thr Val Phe Lys Ser Val Gly Ser Ala Val Val Asp Met Leu Ala Ala
545                 550                 555                 560

Gln Phe Val Tyr Glu Ser Tyr Ile Gly Lys
                565                 570
```

<210> SEQ ID NO 13
<211> LENGTH: 39
<212> TYPE: DNA
<213> ORGANISM: Artificial Sequence
<220> FEATURE:
<223> OTHER INFORMATION: PCR primer

<400> SEQUENCE: 13
ggatccgaat tcatggctgc attaccagta ttcatacca                    39

<210> SEQ ID NO 14
<211> LENGTH: 33
<212> TYPE: DNA
<213> ORGANISM: Artificial Sequence
<220> FEATURE:
<223> OTHER INFORMATION: PCR primer

<400> SEQUENCE: 14
gtcgacttaa caacggctga ggtaagtctc gtg                          33

<210> SEQ ID NO 15
<211> LENGTH: 34
<212> TYPE: DNA

```
<213> ORGANISM: Artificial Sequence
<220> FEATURE:
<223> OTHER INFORMATION: PCR primer

<400> SEQUENCE: 15
gaattcatgg cttccacaac caccgccata acat                                34

<210> SEQ ID NO 16
<211> LENGTH: 34
<212> TYPE: DNA
<213> ORGANISM: Artificial Sequence
<220> FEATURE:
<223> OTHER INFORMATION: PCR primer

<400> SEQUENCE: 16
gtcgacctag ttattttgct gcaaataggt ctca                                34

<210> SEQ ID NO 17
<211> LENGTH: 37
<212> TYPE: DNA
<213> ORGANISM: Artificial Sequence
<220> FEATURE:
<223> OTHER INFORMATION: PCR primer

<400> SEQUENCE: 17
ggatccatgg cttccgcaaa caaagaccaa aaaacca                             37

<210> SEQ ID NO 18
<211> LENGTH: 37
<212> TYPE: DNA
<213> ORGANISM: Artificial Sequence
<220> FEATURE:
<223> OTHER INFORMATION: PCR primer

<400> SEQUENCE: 18
gtcgacctat tttcctatgt atgactcata aacaaac                             37

<210> SEQ ID NO 19
<211> LENGTH: 449
<212> TYPE: PRT
<213> ORGANISM: Morus alba

<400> SEQUENCE: 19

Met Thr His Asn Tyr Ser Gln Leu Pro Phe Ser Ile Cys Arg Pro His
 1               5                  10                  15

Ala Val Ser Leu Gln Pro Lys Thr Ile Phe Pro Ser Ser Pro Ser Thr
            20                  25                  30

Ser Ser Asp Asn Glu Ile Lys Arg Leu Gly His Phe Thr Lys Val Pro
        35                  40                  45

Arg Ser Val Asn Met Glu Asn Leu Arg Asn Gly Tyr Leu Phe Pro Glu
    50                  55                  60

Ile Ser Lys Ala Ala Phe Asp His Thr Gln Lys His Pro Asp Ala Arg
65                  70                  75                  80

Leu Ile Arg Leu Gly Ile Gly Asp Thr Thr Glu Pro Ile Pro Asp Ile
                85                  90                  95

Ile Thr Ser Ala Met Ala Glu Tyr Ala Lys Ala Leu Ser Thr Ile Glu
            100                 105                 110

Gly Tyr Lys Gly Tyr Gly Asp Glu Gln Gly Asn Met Ala Leu Arg Val
        115                 120                 125

Ala Ile Ala Glu Thr Leu Tyr Arg Asn Met Gly Ile Lys Gly Asn Glu
    130                 135                 140
```

```
Val Phe Val Ser Asp Gly Ala Gln Cys Asp Ile Ser Arg Leu Gln Met
145                 150                 155                 160

Leu Leu Gly Ser Asp Val Thr Val Ala Val Gln Asp Pro Ser Phe Pro
            165                 170                 175

Ala Tyr Ile Asp Ser Ser Val Ile Phe Gly Arg Ala Gly Lys Phe Glu
            180                 185                 190

Glu Glu Thr Gly Lys Tyr Gly Asn Ile Val Tyr Met Lys Cys Ser Pro
            195                 200                 205

Glu Asn Asn Phe Phe Pro Asn Leu Ser Ile Thr Arg Lys Thr Asp Val
210                 215                 220

Ile Phe Phe Cys Cys Pro Asn Asn Pro Thr Gly Asn Ala Ala Thr Lys
225                 230                 235                 240

Leu Gln Leu Gln Gln Leu Val Glu Phe Ala Lys Ala Asn Gly Ser Ile
            245                 250                 255

Ile Ile Tyr Asp Ser Ser Tyr Ala Ala Tyr Ile Ser Asp Glu Ser Pro
            260                 265                 270

Arg Ser Ile Tyr Glu Ile Pro Gly Ala Lys Glu Val Ala Ile Glu Val
            275                 280                 285

Ser Ser Phe Ser Lys Phe Ala Gly Phe Thr Gly Val Arg Leu Gly Trp
290                 295                 300

Thr Val Pro Glu Glu Leu Lys Tyr Thr Asn Gly Phe Pro Val Ile
305                 310                 315                 320

Lys Asp Tyr Asp Arg Ile Val Cys Thr Ser Phe Asn Gly Ala Pro Ser
            325                 330                 335

Ile Ser Gln Ala Gly Gly Leu Ala Cys Leu Ser Pro Gln Gly Tyr Glu
            340                 345                 350

Ala Thr Thr Ala Val Ile Asp Tyr Tyr Lys Glu Asn Ala Lys Ile Ile
            355                 360                 365

Ala Asp Thr Phe Arg Ser Val Gly Leu Lys Val Tyr Gly Gly Glu Asn
            370                 375                 380

Ala Pro Tyr Ile Trp Val His Phe Pro Gly Gln Arg Ser Trp Asp Val
385                 390                 395                 400

Phe Asn Glu Ile Leu Ala Lys Thr His Ile Val Thr Ile Pro Gly Ser
            405                 410                 415

Gly Phe Gly Pro Ala Gly Glu Gly Tyr Met Arg Phe Ser Ala Phe Gly
            420                 425                 430

Arg Arg Glu Asn Ile Leu Glu Ala Ser Arg Arg Leu Lys Ser Leu Tyr
            435                 440                 445

Lys

<210> SEQ ID NO 20
<211> LENGTH: 27
<212> TYPE: DNA
<213> ORGANISM: Artificial Sequence
<220> FEATURE:
<223> OTHER INFORMATION: PCR primer

<400> SEQUENCE: 20
ggatccatga cgcataatta ttctcag                                        27

<210> SEQ ID NO 21
<211> LENGTH: 29
<212> TYPE: DNA
```

```
<213> ORGANISM: Artificial Sequence
<220> FEATURE:
<223> OTHER INFORMATION: PCR primer

<400> SEQUENCE: 21
gtcgactcat ttgtaaagag attttagtc                                              29
```

PRODUCTION METHOD FOR L-CYCLIC AMINO ACIDS

TECHNICAL FIELD

The present invention relates to a method of producing an L-cyclic amino acid that is industrially useful.

BACKGROUND ART

L-cyclic amino acids are useful substances as pharmaceutical intermediate raw materials for thrombin inhibitors, HIV protease inhibitors, NMDA receptor antagonists, TNF-α converting enzyme inhibitors, angiotensin converting enzyme inhibitors, anti-inflammatory agents and the like.

As L-cyclic amino acids, amino acids as shown in the following chemical formulae are known, such as, for example, five-membered ring amino acids such as L-proline and L-hydroxyproline, six-membered ring amino acids such as L-pipecolic acid, and four-membered ring amino acids such as azetidine-2-carboxylic acid.

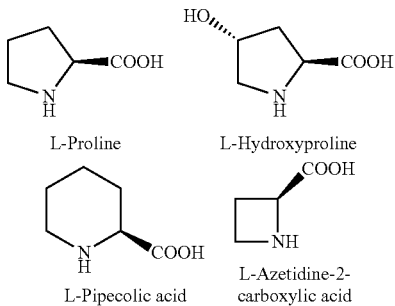

Further, L-thioproline, L-3-morpholinecarboxylic acid, L-3-thiomorpholine carboxylic acid and the like, which are heterocyclic compounds, are also known as useful substances as pharmaceutical intermediate raw materials.

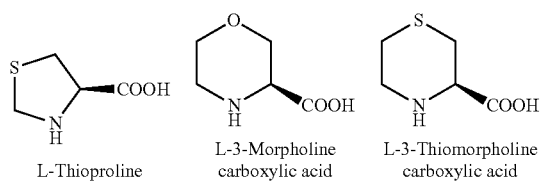 [SMILES: O=C(O)[C@@H]1CSCN1 ; O=C(O)[C@@H]1COCCN1 ; O=C(O)[C@@H]1CSCCN1]

Methods by organic synthesis and biochemical methods are known, as the methods of producing L-cyclic amino acids.

Examples of known methods of producing an L-cyclic amino acid by organic synthesis include the method of producing pipecolic acid proposed by Garcia et al. (Non-patent Document 1). However, it is hard to say that these methods are practically applicable methods in industrial production, both in terms of optical purity and yield.

Examples of known methods of producing an L-cyclic amino acid biochemically include: a method of producing L-pipecolic acid from L-lysine using pyrroline-5-carboxylic acid reductase (EC 1.5.1.2) (Non-patent Document 2); a method of producing L-proline from L-ornithine by ornithine cyclodeaminase (Non-patent Document 3); and methods of producing various types of cyclic amino acids from various types of diamino acids by ornithine cyclodeaminase (Patent Document 1).

The method reported by Fujii et al. (Non-patent Document 2) is a method in which L-lysine is allowed to react with L-lysine 6-aminotransferase to produce $\Delta^1$-piperidine-6-carboxylic acid as an intermediate, and the resulting intermediate is further brought into contact with a reductase to obtain L-pipecolic acid. However, this method is applicable only in the case of using L-lysine as a raw material, and cannot be used for producing other L-cyclic amino acids.

The method reported by Costilow et al. (Non-patent Document 3: Journal of Biological Chemistry (1971)) is a method in which L-ornithine is allowed to react with ornithine cyclase to obtain L-proline. However, Non-patent Document 3 is silent about products other than proline.

Denis et al. have reported (Patent Document 1) methods of obtaining L-pipecolic acid, L-thiomorpholine-2-carboxylic acid, 5-hydroxy-L-pipecolic acid and the like, using ornithine cyclase. However, Patent Document 1 is silent about the yield, the optical purity and the like thereof.

Further, in all of the methods described above, the optical purity of the L-cyclic amino acids as the products depends on the optical purity of the amino acids as raw materials, and thus, it is thought to be difficult to obtain L-cyclic amino acids from racemic raw materials with a high efficiency.

On the other hand, a method in which an L-cyclic amino acid is produced through preparing a cyclic amino acid having a double bond at the 1-position, as an intermediate, is industrially advantageous, because a racemic cyclic amino acid or a diamino acid can be used as a raw material.

For example, an animal-derived or fungus-derived pyrroline-2-carboxylate reductase (EC 1.5.1.1), as an enzyme that reduces a cyclic amino acid having a double bond at the 1-position, has been reported to reduce $\Delta^1$-pyrroline-2-carboxylic acid to produce proline, and to reduce $\Delta^1$-piperidine-2-carboxylic acid to produce pipecolic acid (Non-patent Document 4).

Further, there has been a report that bacteria belonging to the genus *Pseudomonas* metabolize D-lysine to produce L-pipecolic acid, though $\Delta^1$-piperidine-2-carboxylic acid as an intermediate. The report also includes the finding that piperidine-2-carboxylate reductase (EC 1.5.1.21) is responsible for the reduction reaction (Non-patent Document 5).

However, these reports are mere biochemical confirmation of enzyme reactions, and are not examples of industrial production.

In addition, there is also a description that animal-derived enzymes are extremely unstable, and thus, the practical application of industrial production with the use of these enzymes have been difficult.

Patent Document 2 discloses a technique in which a cyclic amino acid having a double bond at the 1-position is obtained as an intermediate, from a diamino acid or a racemic cyclic amino acid, and the resulting cyclic amino acid is reduced using N-methyl-L-amino acid dehydrogenase derived from a bacterium belonging to the genus *Pseudomonas*, to produce an L-cyclic amino acid. Although this method is intended to provide a method of producing an inexpensive and high-purity L-cyclic amino acid, the production of an L-cyclic amino acid with a higher efficiency is required, in order to realize a practical industrial application.

PRIOR ART DOCUMENTS

Patent Documents

Patent Document 1: WO 02/101003
Patent Document 2: JP 4590981 B

Non-Patent Documents

Non-patent Document 1: Concepcion F Garcia et al., Tetrahedron Asymmetry (1995) vol. 6, pp. 2905-2906
Non-patent Document 2: Tadashi Fujii et al., Bioscience Biotechnology Biochem (2002) vol. 66, pp. 1981-1984
Non-patent Document 3: Ralph N Costilow et al., Journal of Biological Chemistry (1971) vol. 246, pp. 6655-6660
Non-patent Document 4: Alton Meister et al., Journal of Biological Chemistry (1957) vol. 229, pp. 789-800
Non-patent Document 5: Cecil W Payton et al., Journal of Bacteriology (1982) vol. 149, pp. 864-871

SUMMARY OF THE INVENTION

Technical Problem

An object of the present invention is to provide a method of industrially producing a high-purity L-cyclic amino acid more inexpensively and with a high efficiency, from a cyclic amino acid having a double bond at the 1-position. Furthermore, the present invention provides a method of industrially producing a high-purity L-cyclic amino acid more inexpensively and with a high efficiency, by obtaining a cyclic amino acid having a double bond at the 1-position, as an intermediate, from an inexpensive diamino acid by reducing the resulting cyclic amino acid in a biochemical method.

Solution to Problem

The use of an imino acid reductase having a catalytic ability to reduce a cyclic amino acid having a double bond at the 1-position to produce an L-cyclic amino acid, which reductase is enzymatically stable and has a high catalytic ability described above, is thought to solve the above-mentioned problems, and to allow for industrially producing a high-purity L-cyclic amino acid more inexpensively and with a high efficiency.

As a result of intensive studies to solve the above-mentioned problems, the present inventors have found out that an imino acid reductase derived from *Arabidopsis thaliana*, *Lathyrus japonicus* or a plant belonging to the genus *Morus* reduces a cyclic amino acid having a double bond at the 1-position, with a catalytic efficiency higher than that of known enzymes.

Further, a cyclic amino acid having a double bond at the 1-position can be efficiently produced from an inexpensive diamino acid using a known enzyme. Therefore, the present inventors have found out that it is possible to industrially produce a high-purity L-cyclic amino acid, which is useful as a pharmaceutical intermediate, more inexpensively and with a high efficiency, from an inexpensive diamino acid, by combining a method of producing a cyclic amino acid having a double bond at the 1-position from a diamino acid and a method of reducing a cyclic amino acid having a double bond at the 1-position with a high catalytic efficiency.

The present invention has been accomplished based on these findings.

Specifically, the present invention is as follows.

[1] A method of producing an L-cyclic amino acid, the method including bringing a cyclic amino acid having a double bond at the 1-position and represented by the following general formula (I):

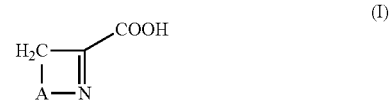

wherein A represents an alkylene chain which has a chain length of from 1 to 4 atoms, which optionally contains at least one hetero atom selected from the group consisting of a sulfur atom, an oxygen atom and a nitrogen atom, in the chain or at the end of the chain, and which optionally has a substituent, into contact with a polypeptide shown in (A), (B) or (C) below, a microorganism or cell having the ability to produce the polypeptide or containing the polypeptide, a processed product of the microorganism or the cell, and/or a culture liquid obtained by culturing the microorganism or the cell and containing the polypeptide, to produce an L-cyclic amino acid represented by the following general formula (II):

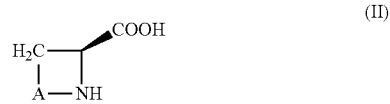

wherein A is the same as defined above:

(A) a polypeptide having the amino acid sequence represented by SEQ ID NO: 2, 4, 6, 8, 10 or 12;

(B) a polypeptide which has the amino acid sequence represented by SEQ ID NO: 2, 4, 6, 8, 10 or 12 except that one or more amino acids are deleted, substituted and/or added, and which has the ability to catalyze the reaction represented by the following formula (1) to produce the L-cyclic amino acid:

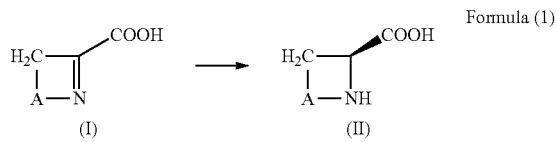

wherein A is the same as defined above;

or (C) a polypeptide which has an amino acid sequence having a sequence identity of 90% or more to the amino acid sequence represented by SEQ ID NO: 2, 4, 6, 8, 10 or 12, and which has the ability to catalyze the reaction represented by the formula (1) to produce the L-cyclic amino acid.

[2] The method of producing an L-cyclic amino acid according to [1], wherein the polypeptide is encoded by a nucleic acid shown in (D), (E) or (F) below: (D) a nucleic acid containing the nucleotide sequence represented by SEQ ID NO: 1, 3, 5, 7, 9 or 11;
  (E) a nucleic acid which contains the nucleotide sequence represented by SEQ ID NO: 1, 3, 5, 7, 9 or 11 except that one or more nucleotides are substituted, deleted and/or added, and which encodes a polypeptide having the ability to catalyze the reaction represented by the formula (1) to produce the L-cyclic amino acid; or
  (F) a nucleic acid which contains a nucleotide sequence that hybridizes with a complementary strand of the nucleotide sequence represented by SEQ ID NO: 1, 3, 5, 7, 9 or 11 under stringent conditions, and which encodes a polypeptide having the ability to catalyze the reaction represented by the formula (1) to produce the L-cyclic amino acid.
[3] A method of producing an L-cyclic amino acid, the method including:
  allowing an acyclic (chain) α, ω-diamino acid represented by the following general formula (III):

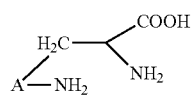
(III)

wherein A represents an alkylene chain which has a chain length of from 1 to 4 atoms, which optionally contains at least one hetero atom selected from the group consisting of a sulfur atom, an oxygen atom and a nitrogen atom, in the chain or at the end of the chain, and which optionally has a substituent,
  to react with an enzyme capable of converting the amino group at the α-position of the diamino acid to a keto group and producing an α-keto acid, to produce a cyclic amino acid having a double bond at the 1-position and represented by the following general formula (I):

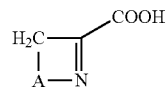
(I)

wherein A is the same as defined above; and
  then producing an L-cyclic amino acid represented by the following general formula (II):

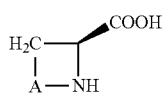
(II)

wherein A is the same as defined above,
  from the resulting cyclic amino acid having a double bond at the 1-position by the method according to [1] or [2].
[4] The method of producing an L-cyclic amino acid according to [3], wherein the enzyme capable of converting the amino group at the a-position of the diamino acid to a keto group and producing an a-keto acid is one or more enzymes selected from the group consisting of a D-amino acid oxidase, an L-amino acid oxidase, a D-amino acid dehydrogenase, an L-amino acid dehydrogenase, a D-amino acid aminotransferase and an L-amino acid aminotransferase.
[5] The method of producing an L-cyclic amino acid according to any one of [1] to [4], wherein the cyclic amino acid having a double bond at the 1-position and represented by the general formula (I) is Δ¹-piperidine-2-carboxylic acid, and the L-cyclic amino acid represented by the general formula (II) is L-pipecolic acid.
[6] A polypeptide shown in (a), (b) or (c) below:
  (a) a polypeptide having the amino acid sequence represented by SEQ ID NO: 4, 6, 8, 10 or 12;
  (b) a polypeptide which has the amino acid sequence represented by SEQ ID NO: 2, 4, 6, 8, 10 or 12 except that one or several amino acids are deleted, substituted and/or added, and which has the ability to catalyze the reaction represented by the following formula (1) to produce the L-cyclic amino acid:

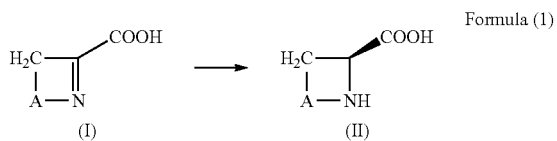
Formula (1)

wherein A represents an alkylene chain which has a chain length of from 1 to 4 atoms, which optionally contains at least one hetero atom selected from the group consisting of a sulfur atom, an oxygen atom and a nitrogen atom, in the chain or at the end of the chain, and which optionally has a substituent;
  or
  (c) a polypeptide which has an amino acid sequence having a sequence identity of 90% or more to the amino acid sequence represented by SEQ ID NO: 2, 4, 6, 8, 10 or 12, and which has the ability to catalyze the reaction represented by the formula (1) to produce the L-cyclic amino acid.
[7] A nucleic acid encoding the polypeptide according to [6].
[8] The nucleic acid according to [7], wherein the nucleic acid is derived from a plant.
[9] The nucleic acid according to [8], wherein the plant is a plant belonging to the genus *Morus* or *Lathyrus japonicus*.
[10] The nucleic acid according to any one of [7] to [9], wherein the nucleic acid is a nucleic acid shown in (d), (e) or (f) below:
  (d) a nucleic acid containing the nucleotide sequence represented by SEQ ID NO: 3, 5, 7, 9 or 11;
  (e) a nucleic acid which contains the nucleotide sequence represented by SEQ ID NO: 1, 3, 5, 7, 9 or 11 except that one or several nucleotides are substituted, deleted and/or added, and which encodes a polypeptide having the ability to catalyze the reaction represented by the formula (1) to produce the L-cyclic amino acid; or
  (f) a nucleic acid which contains a nucleotide sequence that hybridizes with a complementary strand of the nucleotide sequence represented by SEQ ID NO: 1, 3, 5, 7, 9 or 11 under stringent conditions, and which encodes a polypeptide having the ability to catalyze the reaction represented by the formula (1) to produce the L-cyclic amino acid.

[11] A recombinant vector containing the nucleic acid according to any one of [7] to [10].

[12] A transformant containing the recombinant vector according to [11].

[13] An enzyme preparation composition containing a polypeptide shown in (A), (B) or (C) below, a microorganism or cell having the ability to produce the polypeptide or containing the polypeptide, a processed product of the microorganism or the cell, and/or a culture liquid obtained by culturing the microorganism or the cell and containing the polypeptide, wherein the enzyme preparation composition has the ability to produce, from a cyclic amino acid having a double bond at the 1-position and represented by the following general formula (I):

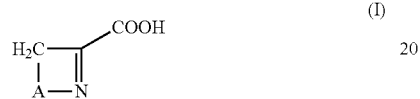

wherein A represents an alkylene chain which has a chain length of from 1 to 4 atoms, which optionally contains at least one hetero atom selected from the group consisting of a sulfur atom, an oxygen atom and a nitrogen atom, in the chain or at the end of the chain, and which optionally has a substituent, an L-cyclic amino acid represented by the following general formula (II):

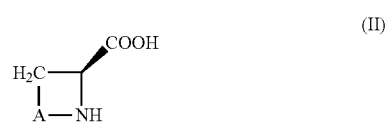

wherein A is the same as defined above:

(A) a polypeptide having the amino acid sequence represented by SEQ ID NO: 2, 4, 6, 8, 10 or 12;

(B) a polypeptide which has the amino acid sequence represented by SEQ ID NO: 2, 4, 6, 8, 10 or 12 except that one or several amino acids are deleted, substituted and/or added, and which has the ability to catalyze the reaction represented by the following formula (1) to produce the L-cyclic amino acid:

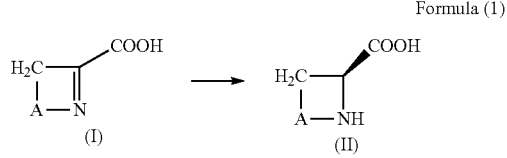

Formula (1)

wherein A is the same as defined above;

or (C) a polypeptide which has an amino acid sequence having a sequence identity of 90% or more to the amino acid sequence represented by SEQ ID NO: 2, 4, 6, 8, 10 or 12, and which has the ability to catalyze the reaction represented by the formula (1) to produce the L-cyclic amino acid.

Advantageous Effects of the Invention

According to present invention, a high-purity L-cyclic amino acid can be produced more efficiently at lower cost, by using an enzyme having a catalytic ability to produce an L-cyclic amino acid by reducing a cyclic amino acid with a double bond at the 1-position, which enzyme is enzymatically stable and has a high catalytic ability described above. Further, it is possible to industrially produce a high-purity L-cyclic amino acid, which is useful as a pharmaceutical intermediate, more inexpensively and with a high efficiency, from an inexpensive diamino acid, by combining a method of producing a cyclic amino acid having a double bond at the 1-position from a diamino acid, and a method of reducing a cyclic amino acid having a double bond at the 1-position with a high catalytic efficiency.

DESCRIPTION OF THE EMBODIMENTS

Figure 1:
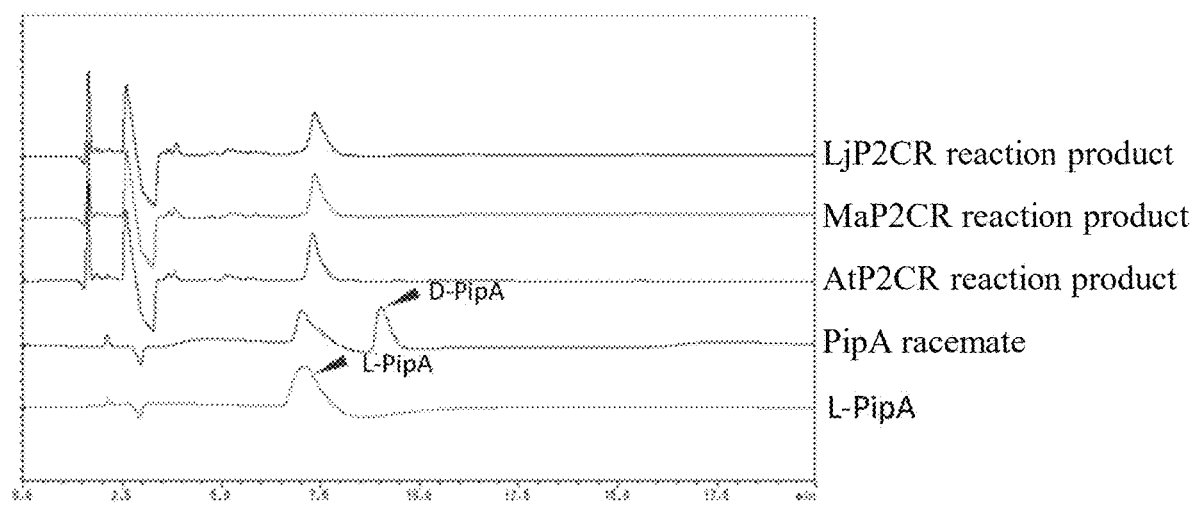
FIG. 1 shows the results of the HPLC analysis of the produced pipecolic acids, performed in the section of (2) Analysis of Enzyme Reaction Products in Example 2.

The present invention will now be described in detail.

In the general formulae (I), (II) and (III) of the present invention, A represents an alkylene chain which has a chain length of from 1 to 4 atoms, which optionally contains at least one hetero atom selected from the group consisting of a sulfur atom, an oxygen atom and a nitrogen atom, in the chain or at the end of the chain, and which optionally has a substituent.

Examples of the alkylene chain include linear or branched alkylene chains having from 1 to 4 carbon atoms, such as —$CH_2$—, —$C_2H_4$—, —$C_3H_6$—, —$C_2H_3CH_3$—, —$C_4H_8$—, —$C_3H_5CH_3$—, and —$CH_2CHCH_3CH_2$—. Among these, a linear alkylene chain having from 2 to 4 carbon atoms, which is capable of forming an L-cyclic amino acid with a five-membered ring, a six-membered ring or a seven-membered ring is preferred. For example, a five-membered ring amino acid such as L-proline is formed when A has two carbon atoms, a six-membered ring amino acid such as L-pipecolic acid is formed when A has three carbon atoms, and a seven-membered ring amino acid such as azepane-2-carboxylic acid is formed when A has four carbon atoms. The chemical formulae of these compounds are shown below.

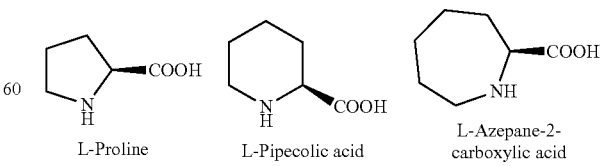

L-Proline    L-Pipecolic acid    L-Azepane-2-carboxylic acid

Further, the alkylene chain may contain at least one hetero atom, such as a sulfur atom, an oxygen atom or a nitrogen atom, in the chain or at the end of the chain. The alkylene chain containing at least one of these hetero atoms forms a heterocyclic ring. The alkylene chain may contain one or more kinds of, or one or more number of, hetero atoms, such as sulfur, oxygen and nitrogen atoms. The alkylene chain preferably contains from 1 to 3 hetero atoms. Examples of the alkylene chain containing at least one hetero atom include —CHOHCH$_2$—, —CH$_2$CHOHCH$_2$—, —SCH$_2$—, —SC$_2$H$_4$—, —SC$_3$H$_6$—, —OCH$_2$—, —OC$_2$H$_4$—, —OC$_3$H$_6$—, —NHCH$_2$—, —NHC$_2$H$_4$—, —NHC$_3$H$_6$—, —NHCH$_2$CHCOOH—, —C$_2$H$_4$NHCO—, —C$_2$H$_4$NHCN—, —C$_2$H$_4$CHCOOH—, —SCH$_2$CHCOOH—, —SC$_2$H$_4$CHCOOH—, and —NHCHCOOHCH$_2$—.

Examples of the L-cyclic amino acid when A is an alkylene chain containing a sulfur atom include thioproline, 3-thiomorpholinecarboxylic acid and [1,4]-thiazepane-3-carboxylic acid. Examples of the L-cyclic amino acid when A is an alkylene chain containing an oxygen atom include 4-oxazolidinecarboxylic acid and 3-morpholinecarboxylic acid. Examples of the L-cyclic amino acid when A is an alkylene chain containing a plurality of nitrogen atoms include piperazine-2-carboxylic acid. The chemical formulae of these compounds are shown below.

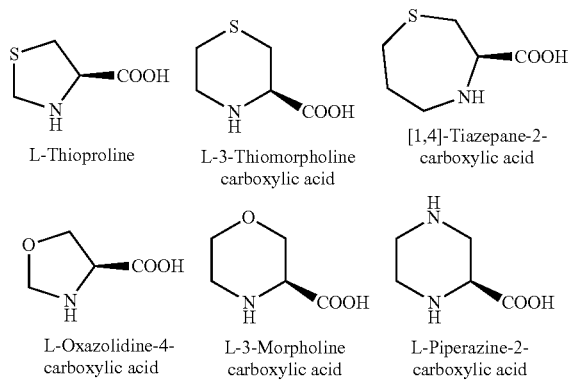

Further, the above described alkylene chain, or the above described alkylene chain containing at least one hetero atom, may have a substituent. The substituent is not particularly limited, and may be any group as long as it does not adversely affect the reaction. Specific examples of the substituent include alkyl groups having from 1 to 4 carbon atoms, aryl groups having from 6 to 12 carbon atoms, alkoxy groups having from 1 to 4 carbon atoms, carboxyl group, halogen groups, cyano group, amino group, nitro group and hydroxyl group, but not particularly limited thereto. The substituent is preferably a hydroxyl group. Examples of the L-cyclic amino acid containing a substituent include hydroxyproline and hydroxypipecolic acid. The chemical formulae of these compounds are shown below.

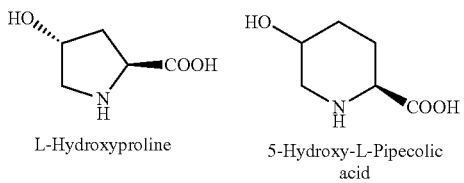 [SMILES: O=C(O)[C@@H]1C[C@@H](O)CN1 ; O=C(O)[C@@H]1CCC(O)CN1]

Among these, A is preferably a linear alkylene chain having from 2 to 4 carbon atoms, and particularly preferably an alkylene chain having three carbon atoms.

1. Imino Acid Reductase

The imino acid reductase to be used in the present invention is an enzyme that catalyzes the reaction represented by the following formula (1):

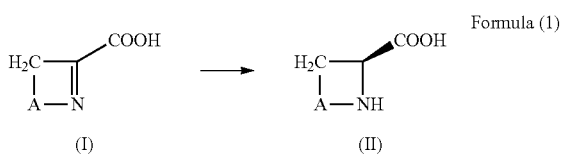

Formula (1)

(wherein A is the same as defined above).

The enzyme that catalyzes the reaction represented by the formula (I) refers to an enzyme which has the ability to produce an L-cyclic amino acid represented by the general formula (II), by being brought into contact with a cyclic amino acid having a double bond at the 1-position represented by the general formula (I). Specifically, the enzyme described above is an imino acid reductase (polypeptide), a microorganism or cell having the ability to produce the polypeptide or containing the polypeptide, a processed product of the microorganism or cell, and/or a culture liquid obtained by culturing the microorganism or cell and containing the polypeptide.

Whether or not the enzyme has "the ability to produce an L-cyclic amino acid represented by the general formula (II) from a cyclic amino acid having a double bond at the 1-position and represented by the general formula (I)" can be confirmed, for example, by the following method. Specifically, in a reaction system containing $\Delta^1$-piperidine-2-carboxylic acid as a substrate, and further containing NAD (P)$^+$ or NAD (P) H as a coenzyme, $\Delta^1$-piperidine-2-carboxylic acid is allowed to react with the enzyme to be measured, to reduce the $\Delta^1$-piperidine-2-carboxylic acid, and the amount of L-pipecolic acid thereby produced is directly measured.

The contact method is not particularly limited, and examples thereof include a method in which the cyclic amino acid having a double bond at the 1-position and represented by the general formula (I) is added to a liquid containing the imino acid reductase, and the resulting mixture is allowed to react at an appropriate temperature (for example, a temperature of from about 10° C. to 45° C.) and at an appropriate pressure (for example, a pressure of about atmospheric pressure). Further, the reaction time is within the range which can be adjusted as appropriate depending on the type of the enzyme, the target product and the like.

In the present invention, an enzyme that catalyzes the reaction (the reaction to reduce $\Delta^1$-piperidine-2-carboxylic acid to produce L-pipecolic acid) represented by the following formula (2) is particularly preferred.

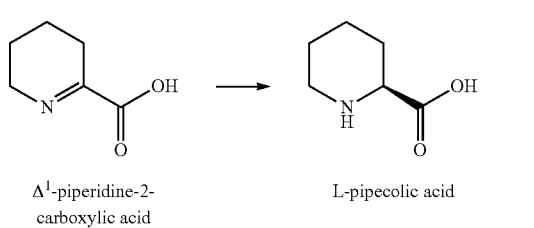

Δ¹-piperidine-2-
carboxylic acid

L-pipecolic acid

Further, the imino acid reductase is preferably an enzyme that reduces the cyclic amino acid having a double bond at the 1-position and represented by the general formula (I) to produce the L-cyclic amino acid represented by the general formula (II), for example, with a reduced nicotinamide adenine nucleotide (NADH) or a reduced nicotinamide adenine dinucleotide phosphate (NADPH) (hereinafter, both of these are sometimes collectively abbreviated as "NAD (P)H") as a coenzyme.

Such an imino acid reductase can be obtained by extraction and purification by a known method, from a plant belonging to the genus *Arabidopsis*, such as *Arabidopsis thaliana*, *Arabidopsis kamchatica* or *Arabidopsis halleri*, a plant belonging to the genus *Morus*, such as *Morus bombycis*, *Morus alba* or *Morus latifolia* Poir, or a plant belonging to the genus *Lathyrus*, such as *Lathyrus japonicus*, *Lathyrus quinquenervius* or *Lathyrus odoratus*.

In particular, the imino acid reductase is preferably an imino acid reductase derived from *Arabidopsis thaliana*, *Morus alba* or *Lathyrus japonicus*. For example, the imino acid reductase obtained by extraction and purification from *Arabidopsis thaliana*, *Morus alba* or *Lathyrus japonicus* is preferred. Further, since the present invention have clarified the sequences of the imino acid reductases derived from *Arabidopsis thaliana*, *Morus alba* and *Lathyrus japonicus*, an imino acid reductase synthesized using any of these sequences by a known method is also preferably used.

The extraction of an enzyme from a plant can be carried out in accordance with a common method of extracting a plant enzyme (for example, the method disclosed in Biochemical Experiments 14, Research methods for Secondary Metabolism in Higher Plants (1981), edited by Ikuzo Uritani, Kensuke Shimura, Michinori Nakamura and Masaru Funatsu, Japan Scientific Societies Press; or in Basic Experiments on Proteins and Enzymes (1981), edited by Takekazu Horio and Jinpei Yamashita, Nankodo Co., Ltd.).

In order to remove residues from the resulting extract, solid-liquid separation means such as filtration and centrifugation are used to prepare a crude enzyme extraction liquid. The purification of the target enzyme from the crude enzyme extraction liquid can be carried out using a known separation and purification method(s). For example, a crude enzyme protein can be obtained from the crude enzyme extraction liquid by a method such as salting-out with ammonium sulfate or organic solvent sedimentation, and further, a purified enzyme can be obtained from the resulting crude enzyme protein, by any appropriate combination of various chromatography methods, such as ion exchange chromatography, gel filtration chromatography and affinity chromatography.

The imino acid reductase to be used in the present invention is specifically one containing a polypeptide consisting of the amino acid sequence represented by SEQ ID NO: 2, 4, 6, 8, 10 or 12, or alternatively, one (hereinafter, sometimes referred to as a "homolog of the imino acid reductase) containing a polypeptide which consists of an amino acid sequence having a high identity to the above-described amino acid sequence (hereinafter, sometimes referred to as a "homolog of the amino acid sequence"), and which has the ability to catalyze the reaction represented by the formula (1) to produce the L-cyclic amino acid (L-cyclic amino acid-producing ability).

More specifically, the imino acid reductase to be used in the present invention is one containing a polypeptide shown in (A), (B) or (C) below:

(A) a polypeptide having the amino acid sequence represented by SEQ ID NO: 2, 4, 6, 8, 10 or 12;

(B) a polypeptide which has the amino acid sequence represented by SEQ ID NO: 2, 4, 6, 8, 10 or 12 except that one or several amino acids are deleted, substituted and/or added, and which has the ability to catalyze the reaction represented by the following formula (1) to produce the L-cyclic amino acid:

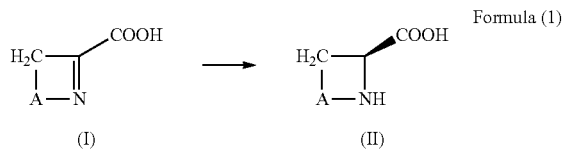

(wherein A is the same as defined above);
or (C) a polypeptide which has an amino acid sequence having a sequence identity of 90% or more to the amino acid sequence represented by SEQ ID NO: 2, 4, 6, 8, 10 or 12, and which has the ability to catalyze the reaction represented by the formula (1) to produce the L-cyclic amino acid.

In the present invention, the homolog of the imino acid reductase having the amino acid sequence represented by SEQ ID NO: 2, 4, 6, 8, 10 or 12, is one containing the polypeptide shown in the above-described (B) or (C).

The polypeptide shown in (B) is a polypeptide which has the amino acid sequence represented by SEQ ID NO: 2, 4, 6, 8, 10 or 12 except that one or several amino acids are deleted, substituted and/or added, and which has the ability to catalyze the reaction represented by the formula (1) to produce the L-cyclic amino acid.

In the case of substitution, a polypeptide which has the above-described amino acid sequence in which one or several amino acids are conservatively substituted is preferred. In the present specification, the expression "one or several amino acids are conservatively substituted" refers to a substation(s) between amino acids having similar chemical properties and the like, and examples thereof include substituting a basic amino acid with a basic amino acid, and substituting an acidic amino acid with an acidic amino acid.

The expression "one or several amino acids" usually refers to from 1 to 100 amino acids, preferably from 1 to 50 amino acids, more preferably from 1 to 20 amino acids, still more preferably from 1 to 10 amino acids, particularly preferably from 1 to 5 amino acids, and most preferably from 1 to 3 amino acids.

The polypeptide shown in (C) is a polypeptide which has an amino acid sequence having a sequence identity of 90% or more to the amino acid sequence represented by SEQ ID NO: 2, 4, 6, 8, 10 or 12, and which has the ability to catalyze the reaction represented by the formula (1) to produce the L-cyclic amino acid. The polypeptide shown in (C) is preferably a polypeptide which has an amino acid sequence having a sequence identity of 80% or more, more preferably 90% or more, still more preferably 95% or more, particularly preferably 98% or more, and most preferably 99% or more, to the full length of the amino acid sequence represented by SEQ ID NO: 2, 4, 6, 8, 10 or 12, and which has the activity to catalyze the reaction represented by the formula (1).

The homology (also referred to as identity or similarity) of an amino acid sequence to another, in the present specification, can be calculated using a homology calculation algorithm, NCBI BLAST (National Center for Biotechnology Information Basic Local Alignment Search Tool), for example, under the following conditions (expected value=10; gap permitted; matrix=BLOSUM62; filtering=OFF). Examples of other algorithms for determining the homology of an amino acid sequence to another include: the algorithm disclosed in Karlin et al., Proc. Natl. Acad. Sci. USA, 90: 5873-5877 (1993) [this algorithm is incorporated into the NBLAST and XBLAST programs (version 2.0) (Altschul et al., Nucleic Acids Res., 25: 3389-3402 (1997))]; the algorithm disclosed in Needleman et al., J. Mol. Biol., 48: 444-453 (1970) [this algorithm is incorporated into the GAP program in the GCG software package]; the algorithm disclosed in Myers and Miller, CABIOS, 4: 11-17 (1988) [this algorithm is incorporated into the ALIGN program (version 2.0) which is a part of the CGC sequence alignment software package]; and the algorithm disclosed in Pearson et al., Proc. Natl. Acad. Sci. USA, 85: 2444-2448 (1988) [this algorithm is incorporated into the FASTA program in the GCG software package]. These algorithms can be preferably used as well.

The imino acid reductase according to the present invention can also be produced by culturing a transformant containing a nucleic acid encoding the imino acid reductase and separating and purifying the imino acid reductase from the resulting culture. The nucleic acid encoding the imino acid reductase according to the present invention may be a DNA or an RNA, or alternatively, a DNA/RNA chimera. Preferably, the nucleic acid may be, for example, a DNA. Further, the nucleic acid may be a double-stranded or single-stranded nucleic acid. In the case of a double-stranded nucleic acid, the nucleic acid may be a double-stranded DNA, a double-stranded RNA or a DNA-RNA hybrid. In the case of a single-stranded nucleic acid, the nucleic acid may be a sense strand (namely, the coding strand), or an antisense strand (namely, the non-coding strand).

The DNA encoding the imino acid reductase according to the present invention may be, for example, a synthesized DNA. The synthesized DNA can be obtained, for example, by: preparing the full-length cDNA of the imino acid reductase directly amplified by Reverse Transcriptase-PCR using, as a template, the total RNA or mRNA fraction prepared from cells or tissues derived from *Arabidopsis thaliana, Morus alba* or *Lathyrus japonicus*; and converting the amplified cDNA by a known method, such as the ODA-LA PCR method, the Gapped duplex method or the Kunkel method, or a modification thereof, using a known kit, such as Mutan™-Super Express Km (manufactured by Takara Bio Inc.) or Mutan™-K (manufactured by Takara Bio Inc). Alternatively, the synthesized DNA can also be obtained by: inserting a fragment of the total RNA or mRNA described above into an appropriate vector to construct a cDNA library; cloning the cDNA from the cDNA library by a method such as colony or plaque hybridization or PCR; and converting the cloned cDNA by any of the methods described above. The vector to be used for the library construction may be a bacteriophage, a plasmid, a cosmid, a phagemid or the like.

Further, the imino acid reductase according to the present invention may be a fusion protein with an affinity polypeptide, for the purpose of facilitating the purification or maintaining the characteristics thereof in a more preferred state. Such a fusion protein may be, for example, a fusion protein with a known affinity polypeptide, such as glutathione-S-transferase (GST), a histidine tag, maltose-binding protein (MBP), an HA tag, a FLAG tag, a biotinylated peptide or green fluorescent protein. Such a fusion protein can be obtained by affinity purification or the like.

In the present invention, a fusion protein with GST is preferred. The polypeptides having the amino acid sequences of SEQ ID NOs: 8, 10 and 12 are fusion proteins in which GST is fused with the polypeptides having the amino acid sequences of SEQ ID NOs: 2, 4 and 6, respectively.

The nucleic acids encoding the polypeptides having the amino acid sequences of SEQ ID NOs: 2, 4, 6, 8, 10 and 12 may be, for example, nucleic acids containing the nucleotide sequences of SEQ ID NOs: 1, 3, 5, 7, 9 and 11, respectively. The nucleic acid encoding the polypeptide having the amino acid sequence represented by SEQ ID NO: 2, 4, 6, 8, 10 or 12 may be a nucleic acid which contains a nucleotide sequence having a high identity to the nucleotide sequence represented by SEQ ID NO: 1, 3, 5, 7, 9 or 11 (hereinafter, sometimes referred to as a "homolog of the nucleic acid"), as long as the nucleic acid encodes a polypeptide having the activity to catalyze the reaction represented by the formula (1). In other words, the nucleic acid encoding the polypeptide may be, for example, a nucleic acid having a nucleotide sequence shown in (D), (E) or (F) below:

(D) a nucleic acid containing the nucleotide sequence represented by SEQ ID NO: 1, 3, 5, 7, 9 or 11;

(E) a nucleic acid which contains the nucleotide sequence represented by SEQ ID NO: 1, 3, 5, 7, 9 or 11 except that one or several nucleotides are substituted, deleted and/or added, and which encodes a polypeptide having the ability to catalyze the reaction represented by the formula (1) to produce the L-cyclic amino acid; or (F) a nucleic acid which contains a nucleotide sequence that hybridizes with a complementary strand of the nucleotide sequence represented by SEQ ID NO: 1, 3, 5, 7, 9 or 11 under stringent conditions, and which encodes a polypeptide having the ability to catalyze the reaction represented by the formula (1) to produce the L-cyclic amino acid.

The homolog of the nucleic acid shown in the above-described (E) may be, for example, a nucleic acid which contains the nucleotide sequence represented by SEQ ID NO: 1, 3, 5, 7, 9 or 11 except that one or several nucleotides are deleted, substituted, inserted and/or added, and which encodes a polypeptide having the activity to catalyze the reaction represented by the formula (1). In the case of substitution, insertion or addition, a nucleic acid which contains the above-described nucleotide sequence in which one or several nucleotides are substituted, inserted or added is preferred. The expression "one or several nucleotides" as used herein refers to, for example, from 1 to 300 nucleotides, preferably from 1 to 150 nucleotides, more preferably from 1 to 60 nucleotides, still more preferably from 1 to 30 nucleotides, particularly preferably from 1 to 15 nucleotides, and most preferably from 1 to 5 nucleotides.

The nucleotide sequences of SEQ ID NOs: 1, 3 and 5 are nucleotide sequences in which the codons of imino acid reductase genes derived from *Arabidopsis thaliana, Morus alba* and *Lathyrus japonicus*, respectively, are optimized for *Escherichia coli* expression. A DNA codon-optimized for the host to be transformed as described above is, of course, also included in the definition of the nucleic acid which encodes a polypeptide having the activity to catalyze the reaction represented by the formula (1) which can be used in the present invention.

The homolog of the nucleic acid shown in the above-described (F) may be, for example, a nucleic acid which contains a nucleotide sequence that hybridizes with a complementary strand of the nucleotide sequence represented by SEQ ID NO: 1, 3, 5, 7, 9 or 11 under stringent conditions, and which encodes a polypeptide having the ability to catalyze the reaction represented by the formula (1) to produce the L-cyclic amino acid. The homolog of the nucleic acid is preferably a nucleic acid which has a nucleotide sequence having a homology (also referred to as identity) of 80% or more, more preferably 90% or more, still more preferably 95% or more, yet still more preferably 98% or more, and most preferably 99% or more, to the nucleotide sequence represented by SEQ ID NO: 1, 3, 5, 7, 9 or 11, and which encodes a polypeptide having the activity to catalyze the reaction represented by the formula (1).

The homology (also referred to as identity) of a nucleotide sequence to another, in the present specification, can be calculated using a homology calculation algorithm, NCBI BLAST (National Center for Biotechnology Information Basic Local Alignment Search Tool), for example, under the following conditions (expected value=10; gap permitted; filtering=ON; match score=1; mismatch score=−3). Preferred examples of other algorithms for determining the homology of a nucleotide sequence to another include the same homology calculation algorithms described above for the amino acid sequence.

The homolog of the nucleic acid shown in the above-described (F) may be a nucleic acid that hybridizes with a complementary strand of the nucleotide sequence represented by SEQ ID NO: 1, 3, 5, 7, 9 or 11 under stringent conditions, as long as the nucleic acid encodes a polypeptide having the activity to catalyze the reaction represented by the formula (1). The "stringent conditions" can be set as appropriate referring to previously reported conditions (for example, Current Protocols in Molecular Biology, John Wiley & Sons, 6.3.16.3.6, 1999). Specifically, the stringent conditions may be, for example, conditions of performing washing once, more preferably two to three times, at salt concentrations and a temperature corresponding to: 60° C., 1×SSC and 0.1% SDS, preferably 0.1×SSC and 0.1% SDS, more preferably 65° C., 0.1×SSC and 0.1% SDS, or 68° C., 0.1×SSC and 0.1% SDS, etc. (highly stringent conditions), which are washing conditions for ordinary Southern hybridization.

Those skilled in the art can obtain the homolog of the nucleic acid as described above, by performing substitution, deletion, insertion and/or addition on the nucleic acid having the nucleotide sequence represented by SEQ ID NO: 1, 3, 5, 7, 9 or 11, as appropriate, to introduce a desired mutation(s), using a method such as site-specific mutagenesis (Nucleic Acids Res. 10, pp. 6487 (1982), Methods in Enzymol. 100, pp. 448 (1983), Molecular Cloning, PCR A Practical Approach, IRL Press, pp. 200 (1991)).

The nucleic acid according to the present invention can encode a polypeptide having the activity to catalyze the reaction represented by the formula (1). In cases where the nucleic acid according to the present invention has the nucleotide sequence represented by SEQ ID NO: 1, 3, 5, 7, 9 or 11, or a nucleotide sequence having a high identity to the nucleotide sequence represented by SEQ ID NO: 1, 3, 5, 7, 9 or 11, the degree of the L-cyclic amino acid-producing ability of an imino acid reductase containing a polypeptide encoded by the nucleic acid can be quantitatively the same as the degree of an imino acid reductase containing a polypeptide having the amino acid sequence represented by SEQ ID NO: 2, 4, 6, 8, 10 or 12, or of an imino acid reductase containing a polypeptide having a homolog of the amino acid sequence. However, the degree of the L-cyclic amino acid-producing ability may vary within a permissible range (for example, from about 0.1 to about 5 times, preferably from about 0.3 to about 3 times the L-cyclic amino acid-producing ability of the imino acid reductase containing a polypeptide having the amino acid sequence represented by SEQ ID NO: 2, 4, 6, 8, 10 or 12, or of the imino acid reductase containing a polypeptide having a homolog of the amino acid sequence).

Further, it is also possible to obtain the amino acid sequence information of the polypeptide having the activity to catalyze the reaction represented by the formula (1), or the nucleotide sequence information of the DNA encoding the same, by performing a homology search against a database, such as DNA Databank of JAPAN (DDBJ), based on the amino acid sequence represented by SEQ ID NO: 2, 4, 6, 8, 10 or 12, or a part thereof, or alternatively, the nucleotide sequence represented by SEQ ID NO: 1, 3, 5, 7, 9 or 11, or a part thereof.

In the production method according to the present invention to be described later, the imino acid reductase may be directly used in the reaction represented by the formula (1). However, it is preferred to use a microorganism or cell having the ability to produce the enzyme, a processed product of the microorganism or cell, and/or a culture liquid obtained by culturing the microorganism or cell and containing the enzyme.

The microorganism or cell having the ability to produce the imino acid reductase according to the present invention may be a microorganism or cell which inherently has the ability to produce the imino acid reductase, or a microorganism or cell to which the above imino acid reductase-producing ability has been imparted by breeding. The life and death of the microorganism or cell do not matter, and, for example, a resting cell or the like can be suitably used. Examples of the type of the microorganism or cell having the ability to produce the imino acid reductase according to the present invention include those described later as examples of the "host microorganism" or "host cell".

Known methods, such as recombinant gene technology (transformation) and mutagenesis can be used, as means for imparting the above imino acid reductase-producing ability by breeding. Examples of the transformation method include: a method of introducing the target DNA; and a method of modifying an expression regulatory sequence, such as a promoter, on the chromosome, to enhance the expression of the target DNA.

Among these, it is preferred to use a microorganism or cell transformed with the DNA encoding the polypeptide according to the present invention described above.

The nucleic acid (DNA) encoding the polypeptide (imino acid reductase) according to the present invention can be cloned, as described above, for example, by PCR using, as a template, a chromosomal DNA derived from *Arabidopsis thaliana, Morus alba* or *Lathyrus japonicus*, and using appropriate primers.

Further, the nucleic acid (DNA) encoding the polypeptide (imino acid reductase) according to the present invention can be cloned, as described above, for example, by: preparing the full-length cDNA of the imino acid reductase directly amplified by RT-PCR using, as a template, the total RNA or mRNA derived from *Arabidopsis thaliana, Morus alba* or *Lathyrus japonicus*; and then performing PCR using appropriate primers.

For example, the DNA encoding the polypeptide according to the present invention which has been obtained as described above can be operably inserted into a known expression vector, to provide a polypeptide gene expression vector according to the present invention. Thereafter, a host microorganism or cell can be transformed with the resulting expression vector to obtain a transformant into which the DNA encoding the polypeptide according to the present invention has been introduced. The transformant can also be obtained by operably incorporating the DNA encoding the polypeptide according to the present invention into the chromosomal DNA of a host, by a method such as homologous recombination.

In the present specification, the term "expression vector" refers to a genetic element used for incorporating a polynucleotide encoding a protein with a desired function thereinto and introducing the genetic element into a host microorganism or cell, so as to allow the protein with a desired function to be replicated and expressed in a host microorganism or cell. The expression vector may be, for example, a plasmid, a virus, a phage or a cosmid, but not limited thereto. The expression vector is preferably a plasmid.

In the present specification, the term "transformant" refers to a microorganism or cell into which the target gene has been introduced using the expression vector as described above or the like, and thus has become capable of exhibiting a desired trait related to a protein with a desired function.

Specific examples of the method of producing a transformant include, but not limited to: a method in which the DNA encoding the polypeptide according to the present invention is introduced into a plasmid vector, a phage vector or a virus vector that can stably exist in a host microorganism or host cell, and then the constructed expression vector is introduced into the host microorganism or host cell; and a method in which the DNA is directly introduced into the host genome, to allow the genetic information thereof to be transferred and translated. In these methods, it is preferred that a promoter suitable in the host be linked upstream of the 5'-side of the DNA, and it is more preferred that a suitable terminator be further linked downstream of the 3'-side of the DNA. Such a promoter and a terminator are not particularly limited, as long as they are a promoter and a terminator known to function in a cell used as a host. For example, vectors, promoters and terminators described in detail in "Fundamental Microbiology, Vol. 8, Genetic Engineering, Kyoritsu Shuppan Co., Ltd." can be used.

The host microorganism to be transformed for the expression of the imino acid reductase according to the present invention is not particularly limited, as long as the host itself does not adversely affect the raw material or the intermediate product. Examples of the host microorganism include the following microorganisms:

bacteria belonging to the genera *Escherichia, Bacillus, Pseudomonas, Serratia, Brevibacterium, Corynebacterium, Streptococcus, Lactobacillus* and the like, whose host-vector systems have been established;

actinomycetes belonging to the genera *Rhodococcus, Streptomyces* and the like, whose host-vector systems have been established;

yeasts belonging to the genera *Saccharomyces, Kluyveromyces, Schizosaccharomyces, Zygosaccharomyces, Yarrowia, Trichosporon, Rhodosporidium, Hansenula, Pichia, Candida* and the like, whose host-vector systems have been established; and fungi belonging to the genera *Neurospora, Aspergillus, Cephalosporium, Trichoderma* and the like, whose host-vector systems have been established.

The procedure for producing a transformant, the method of constructing a recombinant vector compatible with the host, and the method of culturing the host can be carried out in accordance with techniques conventionally used in the fields of molecular biology, bioengineering and genetic engineering (such as the methods described in Molecular Cloning).

Specific examples of preferred host microorganisms, and of preferred transformation methods, vectors, promoters and terminators for each microorganism will be described below. However, the present invention is not limited to these examples.

For the genus *Escherichia*, particularly for *Escherichia coli*, examples of preferred plasmid vectors include pBR and pUC-based plasmids, and examples of preferred promotors include promoters derived from lac (β-galactosidase), trp (tryptophan operon), tac, trc (a fusion of lac and trp), PL and PR of phage X and the like. Further, examples of preferred terminators include terminators derived from trpA, phages and rrnB ribosomal RNA.

For the genus *Bacillus*, examples of preferred vectors include pUB110-based plasmids and pC194-based plasmids, which can be integrated into the chromosome. Examples of preferred promoters and terminators include those of the genes of enzymes, such as alkali proteases, neutral proteases and α-amylases.

For the genus *Pseudomonas*, examples of preferred vectors include: common host-vector systems established in *Pseudomonas putida, Pseudomonas cepacia* and the like; and a broad-host-range vector, pKT240 (containing genes required for autonomous replication and derived from RSF1010, etc.) based on the TOL plasmid, which is a plasmid involved in the decomposition of toluene compounds (Gene, 26, 273-82 (1983)).

For the genus *Brevibacterium*, particularly for *Brevibacterium lactofermentum*, examples of preferred vectors include plasmid vectors such as pAJ43 (Gene, 39, 281 (1985)). Further, various types of promoters and terminators used in *Escherichia coli* can be used.

For the genus *Corynebacterium*, particularly for *Corynebacterium glutamicum*, examples of preferred vectors include plasmid vectors such as pCS11 (JP 57-183799A) and pCB101 (Mol. Gen. Genet. 196, 175 (1984)).

For the genus *Saccharomyces*, particularly for *Saccharomyces cerevisiae*, examples of preferred vectors include YRp-based plasmids, YEp-based plasmids, YCp-based plasmids and YIp-based plasmids. Further, promoters and terminators of the genes of various types of enzymes, such as alcohol dehydrogenase, glyceraldehyde-3-phosphate dehydrogenase, acid phosphatase, β-galactosidase, phosphoglycerate kinase and enolase can be used.

For the genus *Schizosaccharomyces*, examples of preferred vectors include plasmid vectors derived from *Schizosaccharomyces pombe*, disclosed in Mol. Cell. Biol. 6, 80 (1986). In particular, pAUR224 is commercially available from Takara Bio Inc., and can be easily used.

In the genus *Aspergillus, Aspergillus niger, Aspergillus oryzae* and the like are most extensively studied species among fungi. Plasmids and integration into the chromosome are applicable to these species, and promoters derived from extracellular protease and amylase genes can be used (Trendsin Biotechnology 7, 283-287 (1989)).

Host-vector systems other than those described above have also been established in various types of microorganisms, and these systems can be used as appropriate.

Further, various host-vector systems have been established in plants and animals, in addition to microorganisms. In particular, a system for allowing the expression of a large amount of foreign protein in an animal such as an insect (for example, silkworm) (Nature 315, 592-594 (1985)), or in a plant such as rapeseed, corn or potato; and a system using an *Escherichia coli* cell-free extract or a cell-free protein synthesis system from wheat germ or the like; have been established, and can be suitably used.

The processed product of the microorganism or cell having the ability to produce the imino acid reductase according to the present invention may be, for example: a cell preparation, such as a product prepared by treating the microorganism or cell with an organic solvent such as acetone, dimethyl sulfoxide (DMSO) or toluene or with a surfactant, a product prepared by freeze drying the microorganism or cell, or a product prepared by physically or enzymatically disrupting the microorganism or cell; a product prepared by extracting the enzyme fraction in the microorganism or cell as a crude product or a purified product; or a product prepared by immobilizing any of the above on a carrier typified by a polyacrylamide gel, a carrageenan gel or the like.

The culture liquid which is obtained by culturing the microorganism or cell having the ability to produce the imino acid reductase according to the present invention, and which contains the enzyme, may be, for example: a suspension of the microorganism or cell in a liquid medium; or, when the cell is a secretory expressive cell, a supernatant obtained by removing the cell by centrifugation or the like, or a concentrate thereof.

The imino acid reductase according to the present invention can be used particularly suitably in the method of reducing $\Delta^1$-piperidine-2-carboxylic acid to produce L-pipecolic acid.

In cases where the transformant to be used in the present invention is a prokaryote such as *Escherichia coli*, or a eukaryote such as yeast, the culture medium for culturing such a microorganism may be either a natural culture medium or a synthetic culture medium, as long as the medium contains a carbon source, a nitrogen source, an inorganic salt etc. which can be utilized by the microorganism, and allows for efficiently culturing the transformant. The culture is preferably carried out under aerobic conditions, such as shaking culture, deep-aerated stirring culture, etc. The culture temperature is usually from 15 to 40° C., and the culture time is usually from 16 hours to 7 days. During the culture, the pH is maintained within the range of from 3.0 to 9.0. The adjustment of the pH is carried out using an inorganic or organic acid, an alkali solution, urea, calcium carbonate, ammonia or the like. If necessary, an antibiotic such as ampicillin or tetracycline may be added to the culture medium during the culture.

To isolate and purify the above-described imino acid reductase from the culture of the transformant, an ordinary method of isolating and purifying a protein can be used.

For example, in cases where the above-described imino acid reductase is expressed in a state dissolved in the cells, the cells are collected by centrifugation after the completion of the culture, suspended in an aqueous buffer solution, and then disrupted using a sonicator, a French press, a Manton-Gaulin Homogenizer, a Dyno-Mill or the like, to obtain a cell-free extract. From the supernatant obtained by centrifuging the cell-free extract, a purified standard can be obtained using, singly or in combination, ordinary methods of isolating and purifying proteins, which methods are, namely: solvent extraction; salting-out by ammonium sulfate or the like; desalting; organic solvent sedimentation; anion-exchange chromatography using a resin such as dimethylaminoethyl (DEAE)-Sepharose or DIAION HPA-75 (manufactured by Mitsubishi Chemical Corporation); cation-exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatographic focusing; and electrophoresis such as isoelectric focusing electrophoresis.

Further, in cases where the above-described imino acid reductase is expressed in the cells in a state of forming an insoluble body, the cells are collected, disrupted and then centrifuged, in the same manner as described above, to obtain the sediment fraction. After recovering the imino acid reductase from the thus obtained sediment fraction by an ordinary method, the insoluble body of the N-methyl-L-amino acid dehydrogenase is solubilized with a protein denaturant. The resulting solubilized liquid is diluted to a thin solution which does not contain the protein denaturant or in which the concentration of the protein denaturant is low enough to the extent that the N-methyl-L-amino acid dehydrogenase is not denatured, or is dialyzed, so as to allow the imino acid reductase to be folded into a normal three-dimensional structure. Thereafter, a purified standard can be obtained by the same isolation and purification method(s) as described above.

2. Composition According to the Present Invention

The composition (enzyme preparation) according to the present invention is a composition containing the imino acid reductase according to the present invention, a microorganism or cell having the ability to produce the enzyme, a processed product of the microorganism or cell, and/or a culture liquid obtained by culturing the microorganism or cell and containing the enzyme, wherein the composition has the above-described L-cyclic amino acid-producing ability. The composition according to the present invention is useful, because the use thereof as a catalyst enables to industrially produce a high-purity L-cyclic amino acid more inexpensively and with a high efficiency.

The composition according to the present invention may contain, in addition to an active ingredient (such as the enzyme), an excipient, a buffer, a suspending agent, a stabilizer, a preservative, an antiseptic, saline and/or the like. Lactose, sorbitol, D-mannitol, white sugar or the like can be used as the excipient. A phosphate, a citrate, an acetate or the like can be used as the buffer. Propylene glycol, ascorbic acid or the like can be used as the stabilizer. Phenol, benzalkonium chloride, benzyl alcohol, chlorobutanol, methylparaben or the like can be used as the preservative. Benzalkonium chloride, paraoxybenzoic acid, chlorobutanol or the like can be used as the antiseptic.

3. Method of Producing L-Cyclic Amino Acid

The present invention provides a method of producing an L-cyclic amino acid, the method including bringing a cyclic amino acid having a double bond at the 1-position and represented by the following general formula (I):

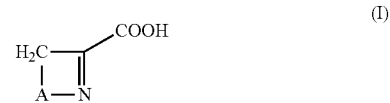

(I)

(wherein A is the same as defined above)
into contact with the imino acid reductase according to the present invention, to produce an L-cyclic amino acid represented by the following general formula (II):

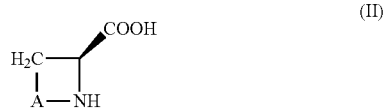

(II)

(wherein A is the same as defined above).

At the time of bringing the cyclic amino acid having a double bond at the 1-position and represented by the general formula (I) into contact with the imino acid reductase according to the present invention, the cyclic amino acid having a double bond at the 1-position and represented by the general formula (I) is brought into contact with the imino acid reductase according to the present invention which has been purified or crudely purified, a microorganism or cell having the ability to produce the imino acid reductase according to the present invention (such as a transformant containing a DNA encoding the polypeptide according to the present invention), a processed product of the microorganism or cell, and/or a culture liquid obtained by culturing the microorganism or cell and containing the enzyme, to reduce the cyclic amino acid, whereby the L-cyclic amino acid represented by the general formula (II) can be produced.

While the imino acid reductase according to the present invention may be directly used in the reaction, it is preferred to use a microorganism or cell having the ability to produce the enzyme, a processed product of the microorganism or cell, and/or a culture liquid obtained by culturing the microorganism or cell and containing the enzyme. Among these, it is preferred to use a transformant containing a DNA encoding the polypeptide according to the present invention.

The amount(s) of the microorganism or cell, the processed product of the microorganism or cell and/or the culture liquid obtained by culturing the microorganism or cell and containing the enzyme, to be added to the reaction liquid is/are as follows. In the case of using the microorganism or cell, the microorganism or cell is added in such an amount that the concentration of the microorganism or cell in the reaction liquid is usually within the range of from about 0.1 w/v % to 50 w/v %, and preferably from 0.1 w/v % to 10 w/v %, in terms of wet cell weight. In the case of using the processed product or the culture liquid, the specific activity of the enzyme is determined, and the processed product or the culture liquid is added in such an amount that the above-described concentration of the microorganism or cell is achieved at the time of the addition, based on the specific activity. The "w/v %" as used herein refers to weight/volume %.

The contact method (reaction method) is not particularly limited, and a method can be used in which the cyclic amino acid having a double bond at the 1-position and represented by the general formula (I), which serves as a substrate, is added to a liquid containing the imino acid reductase according to the present invention, and the resulting mixture is allowed to react at an appropriate temperature and at an appropriate pressure (for example, a pressure of about atmospheric pressure). Further, the reaction time can be adjusted as appropriate, depending on the type of the enzyme, the target product and the like.

The cyclic amino acid having a double bond at the 1-position and represented by the general formula (I), which serves as a reaction substrate, is usually used within such a range that the concentration of the substrate in the reaction liquid is from 0.0001 w/v % to 90 w/v %, and preferably from 0.01 w/v % to 30 w/v %. The reaction substrate may be added all at once at the start of the reaction. However, from the viewpoints of reducing the impact when the substrate inhibition by the enzyme occurred and improving the accumulated concentration of the resulting product, it is preferred to add the reaction substrate continuously or intermittently.

Further, the reaction (reduction reaction) described above is preferably carried out in the presence of a coenzyme. The coenzyme is preferably NAD(P)$^+$ or NAD(P)H. The "NAD(P)$^+$" as used herein refers to oxidized nicotinamide adenine nucleotide (NAD) or oxidized nicotinamide adenine dinucleotide phosphate (NADP).

The coenzyme is added such that the concentration thereof in the reaction liquid is usually from 0.001 mmol/L to 100 mmol/L, and preferably from 0.01 mmol/L to 10 mmol/L.

In the case of adding the coenzyme, it is preferred to regenerate NAD(P)$^+$ produced from NAD(P)H, to NAD(P)H, from the viewpoint of improving the production efficiency. Examples of the regeneration method include: <1> a method in which the ability of a host microorganism itself to reduce NAD(P)$^+$ is utilized; <2> a method in which a microorganism having the ability to produce NAD(P)H from NAD(P)$^+$, or a processed product thereof, or alternatively, an enzyme (regeneration enzyme) which can be used for the regeneration of NAD(P)H, such as glucose dehydrogenase, formate dehydrogenase, alcohol dehydrogenase, an amino acid dehydrogenase, or an organic acid dehydrogenase (such as malate dehydrogenase), is added to the reaction system; and <3> a method in which a gene of any of the-above-described regeneration enzymes which can be used for the regeneration of NAD(P)H, is introduced into a host, simultaneously with the DNA of the present invention, at the time of producing the transformant.

In the method <1> above, among the above-mentioned methods, it is preferred to add glucose, ethanol, formic acid or the like, to the reaction system. In the method <2> above, it is possible to use: a microorganism containing any of the-above-described regeneration enzymes; a microorganism transformed with a DNA encoding any of the the-above-described regeneration enzymes; a cell-processed product, such as a product prepared by treating the cells of the microorganism with acetone, a product prepared by freeze drying the cells, or a product prepared by physically or enzymatically disrupting the cells; a product prepared by extracting the enzyme fraction as a crude product or a purified product; or a product prepared by immobilizing any of the above on a carrier typified by a polyacrylamide gel, a carrageenan gel or the like. A commercially available enzyme may also be used.

In this case, specifically, the regeneration enzyme is added in such an amount that the enzyme activity of the regeneration enzyme is usually from 0.01 times to 100 times, and preferably about from 0.01 times to 10 times the enzyme activity of the imino acid reductase.

Further, it is also necessary to add a compound which serves as a substrate of the regeneration enzyme, for example, glucose in the case of using a glucose dehydrogenase, formic acid in the case of using a formate dehydrogenase, or ethanol or isopropanol in the case of using an alcohol dehydrogenase. Such a compound is added usually in amount of from 1 to 10 molar times, and preferably from 1.0 to 1.5 molar times the amount of a dicarbonyl group-containing compound, which is a reaction raw material.

In the method <3> above, it is possible to use: a method in which the DNA of the imino acid reductase and the DNA of any of the the-above-described regeneration enzymes are incorporated into the chromosome; a method in which both the DNAs are introduced into a single vector, followed by transforming a host by the vector; or a method in which the respective DNAs are introduced into separate vectors, followed by transforming a host by the vectors. However, in the case of using the method in which the respective DNAs are introduced into separate vectors, followed by transforming a host by the vectors, the vectors need to be selected taking into consideration the possibility that both the vectors may be incompatible with each other.

In the case of introducing a plurality of genes into a single vector, it is also possible to use a method of linking the regions involved in expression regulation, such as promoters and terminators, to the respective genes, or a method of allowing the genes to be expressed as an operon including a plurality of cistrons, such as lactose operon.

The reaction (reduction reaction) described above is preferably carried out in an aqueous medium containing the reaction substrate and the transformant as well as any of various types of coenzymes to be added as necessary and a regeneration system thereof, or in a mixture of the aqueous medium and an organic solvent.

The aqueous medium may be, for example, water or a buffer solution. As the organic solvent, it is possible to use a water-soluble organic solvent in which the cyclic amino acid having a double bond at the 1-position and represented by the general formula (I), as the reaction substrate, is highly soluble, such as methanol, ethanol, 1-propanol, 2-propanol, 1-butanol, tert-butanol, tetrahydrofuran, acetone or dimethyl sulfoxide. It is also possible to use a water-insoluble organic solvent or the like which is effective, for example, for removing reaction byproducts, such as ethyl acetate, butyl acetate, toluene, chloroform, n-hexane and the like.

While reaction conditions can be adjusted as appropriate, depending on the type of the enzyme used, the target product and the like, the reaction (reduction reaction) is carried out usually at a reaction temperature of from 4 to 60° C., preferably from 10 to 50° C., and usually at a pH of from 4 to 11, preferably from 5 to 10. The reaction time is usually from about one hour to 72 hours.

The reaction (reduction reaction) can also be carried out using a membrane reactor or the like.

After the completion of the reaction (reduction reaction), the L-cyclic amino acid represented by the general formula (II), which is produced by the reaction, can be separated by a separation or purification method known to those skilled in the art, such as centrifugation or a membrane treatment, to separate cells and proteins in the reaction liquid. Thereafter, the L-cyclic amino acid can be purified by any appropriate combination of: extraction by an organic solvent such as ethyl acetate or toluene; distillation; column chromatography using an ion exchange resin or silica gel; crystallization at the isoelectric point; and crystallization with a monohydrochloride, a dihydrochloride, a calcium salt or the like.

Further, the cyclic amino acid having a double bond at the 1-position and represented by the general formula (I), as the substrate, can be produced by a known method, such as a method by organic synthesis or a biochemical method, from a diamino acid or a racemic cyclic amino acid. Industrially, it is preferred to produce the cyclic amino acid from a diamino acid, from the viewpoints of cost and handleability. The diamino acid is preferably an acyclic α, ω-diamino acid.

In the case of producing the above-described cyclic amino acid from an acyclic α, ω-diamino acid, if the amino group at the α-position of the α, ω-diamino acid is converted to a keto group to produce an α-keto acid, as shown in the following reaction formula, the α-keto acid undergoes non-enzymatic cyclodehydration to form a cyclic amino acid having a double bond at the 1-position.

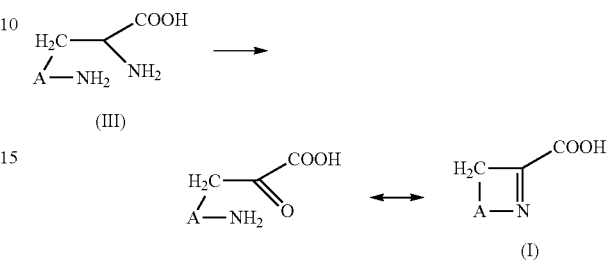

(In the above formula, A is the same as defined above.)

Since the α-keto acid produced by the oxidation of the amino group at the α-position of the α, ω-diamino acid, and the cyclic amino acid having a double bond at the 1-position, are usually present in the aqueous medium as an equilibrium mixture, these compounds are regarded as equivalent. Accordingly, the cyclic amino acid having a double bond at the 1-position, $\Delta^1$-piperidine-2-carboxylic acid, the α-keto acid produced by the oxidation of the amino group at the α-position of the α, ω-diamino acid and the cyclic amino acid having a double bond at the 1-position, or the α-keto acid produced by the oxidation of the amino group at the α-position of the α, ω-diamino acid, can be added to, or incorporated into, the reaction (reduction reaction) system of the present invention, and all of these embodiments are encompassed in the present invention.

In the case of biochemically producing the cyclic amino acid having a double bond at the 1-position from the α, ω-diamino acid, any enzyme can be used without particular limitation, as long as it is capable of converting the amino group at the α-position of the α, ω-diamino acid to a keto group and producing an α-keto acid. The enzyme to be used may be, for example, an amino acid oxidase such as a D-amino acid oxidase or an L-amino acid oxidase, an amino acid dehydrogenase such as a D-amino acid dehydrogenase or an L-amino acid dehydrogenase, or an amino acid aminotransferase such as a D-amino acid aminotransferase or an L-amino acid aminotransferase.

Among these, an enzyme having a wide range of substrate specificity is preferred. Specifically, an L-amino acid oxidase disclosed in Enzyme and Microbial Technology vol. 31 (2002) p 77-87, a D-amino acid oxidase manufactured by Sigma-Aldrich Co. LLC. or the like is preferred.

When the amino acid oxidase, the amino acid dehydrogenase or the amino acid aminotransferase described above is an enzyme that reacts only with a diamino acid, and is one that corresponds to a coenzyme which can be used in the reduction reaction of the present invention, the enzyme can serve as a substitute system of the coenzyme regeneration system, and thus is preferred. That is, when NAD(P)H is used as a coenzyme in the reduction reaction of the present invention, NAD(P)H is converted to NAD(P)$^+$ as reduction proceeds in the present reaction. Meanwhile, the resulting NAD(P)$^+$ can be utilized to be converted to NAD(P)H, at the time of producing the cyclic amino acid having a double bond at the 1-position from the diamino acid, and thus is preferred.

In cases where any of various amino acid oxidases is used at the time of producing the cyclic amino acid having a double bond at the 1-position from the diamino acid, hydrogen peroxide is generated associated with the reaction, which possibly adversely affects the reaction, such as causing a decrease in enzyme activity. Therefore, it is also preferred to use another enzyme for the purpose of removing hydrogen peroxide. The enzyme for removing hydrogen peroxide is not particularly limited, as long as the enzyme reacts with hydrogen peroxide. Specifically, a catalase or a peroxidase is preferred. The enzyme that reacts with hydrogen peroxide is used in such an amount that the activity thereof is usually within the range of from 0.01 times to one million times, and preferably from 0.1 times to 100,000 times the activity of the amino acid oxidase, but not particularly limited thereto as long as the generated hydrogen peroxide can be efficiently removed.

Further, in the case of using an amino acid oxidase, the activity thereof can be enhanced by using flavin adenine dinucleotide (FAD) as a coenzyme. FAD is used in such an amount that the concentration thereof in the reaction liquid is usually within the range of from 0.00001 to 100 millimolar concentration, and preferably from 0.001 to 10 millimolar concentration.

In the case of using the diamino acid as the reaction substrate, the concentration of the substrate is usually within the range of from 0.01 to 90% w/v, and preferably from 0.1 to 30% w/v.

The method of biochemically producing the cyclic amino acid having a double bond at the 1-position from the diamino acid is not particularly limited, and a known method can be used.

For example, a method can be used in which the diamino acid as the reaction substrate is added to a liquid containing the above-described enzyme, and the resulting mixture is allowed to react at an appropriate temperature and at an appropriate pressure (for example, a pressure of about atmospheric pressure).

The diamino acid as the reaction substrate is usually used within such a range that the concentration of the substrate in the reaction liquid is from 0.01 w/v % to 90 w/v %, and preferably from 0.1 w/v % to 30 w/v %. The reaction substrate may be added all at once at the start of the reaction. However, from the viewpoints of reducing the impact when the substrate inhibition by the enzyme occurred and improving the accumulated concentration of the resulting product, it is preferred to add the reaction substrate continuously or intermittently.

The above-described reaction is carried out usually at a reaction temperature of from 4 to 60° C., preferably from 10 to 50° C., and usually at a pH of from 4 to 11, preferably from 5 to 10. The reaction time is usually from about one hour to 72 hours.

In the case of using an amino acid oxidase, the reaction is carried out under the conditions which allow the reaction liquid to be sufficiently mixed with oxygen gas or air, in order to supply oxygen required for the reaction. For example, the speed of shaking or rotating the reaction vessel may be increased, or oxygen gas or air may be passed through the liquid. Oxygen gas or air is passed through the liquid at a speed of usually within the range of from 0.1 vvm to 5.0 vvm, and preferably from 0.1 vvm to 1.0 vvm.

The reaction can also be carried out using a membrane reactor or the like.

After the completion of the above-described reaction, the cyclic amino acid having a double bond at the 1-position and represented by the general formula (I), which is produced by the reaction, can be separated by a separation or purification method known to those skilled in the art, such as centrifugation or a membrane treatment, to separate cells and proteins in the reaction liquid. Thereafter, the cyclic amino acid can be purified by any appropriate combination of: extraction by an organic solvent such as ethyl acetate or toluene; distillation; column chromatography using an ion exchange resin or silica gel; crystallization at the isoelectric point; and crystallization with a monohydrochloride, a dihydrochloride, a calcium salt or the like.

In the present invention, after obtaining the cyclic amino acid having a double bond at the 1-position, the resulting amino acid can be separated and purified, and then subjected to the subsequent step of obtaining the L-cyclic amino acid, or alternatively, the resulting amino acid can be subjected to the subsequent step of obtaining the L-cyclic amino acid, without being separated and purified. Further, the step of obtaining the cyclic amino acid having a double bond at the 1-position, and the step of obtaining the L-cyclic amino acid can be carried out in separate reactors, or alternatively, both the steps can be carried out in the same reactor.

EXAMPLES

The present invention will now be described in further detail by way of Examples. It is noted, however, that the present invention is in no way limited to these Examples.

In the following Examples and Reference Examples, "M" refers to "mol/L", "w/v" refers to "weight/volume" "DMSO" refers to "dimethyl sulfoxide" "ETDA" refers to "ethylenediaminetetraacetic acid", "PTG" refers to "isopropyl-β-thiogalactopyranoside, "PipC2" refers to "$\Delta^1$-piperidine-2-carboxylic acid" and "PipA refers to "pipecolic acid".

<Example 1> (Cloning of Plant-Derived Imine Reductase Genes)

(1) Amplification of Target Genes from Plants

The total RNA was extracted from each of *Arabidopsis thaliana* and *Lathyrus japonicus* which had been grown for about one month after germination. Further, the total RNA was extracted from the leaves of *Morus alba* which had been grown for about one month after germination. The extraction was carried out using RNeasy Plant Mini Kit (manufactured by QIAGEN, Inc.). The operation was carried out at room temperature, with reference to the protocol described in the kit. The cDNA was synthesized from each resulting total RNA, using ReverTra Ace (registered trademark) qPCR RT Master Mix with gDNA Remover (manufactured by TOYOBO Co., Ltd.). Based on the resulting cDNA library, a database of genes expressed in each plant was constructed.

Each resulting cDNA was used as a template to carry out a PCR reaction. Primers used for the PCR were prepared as shown in the following table. Restriction enzymes were added to the N- and C-terminals of the primers, as restriction enzyme recognition sites for insertion into a vector for expression in *Escherichia coli*.

TABLE 1

| SEQ ID NO: | Sequence name | Sequence | Restriction enzyme |
|---|---|---|---|
| 13 | AtP2CR-FW | GGATCCGAATTCATGGCTGCATTACCAGTATTCATACCA | BamHI, EcoRI |
| 14 | AtP2CR-RV | GTCGACTTAACAACGGCTGAGGTAAGTCTCGTG | SalI |
| 15 | MaP2CR-FW | GAATTCATGGCTTCCACAACCACCGCCATAACAT | BamHI |
| 16 | MaP2CR-RV | GTCGACCTAGTTATTTTGCTGCAAATAGGTCTCA | SalI |
| 17 | LjP2CR-FW | GGATCCATGGCTTCCGCAAACAAAGACCAAAAAACCA | BamHI |
| 18 | LjP2CR-RV | GTCGACCTATTTTCCTATGTATGACTCATAAACAAAC | SalI |

The PCR was carried out based on the protocol of TaKaRa Ex Taq (registered trademark) Hot Start Version (manufactured by Takara Bio Inc.). The PCR reaction mixture was as prepared to a total volume of 20 µL, containing: 0.1 µL of Ex Taq HS; 2 µL of 10×Ex Tag Buffer; 1.6 µL of dNTP mixture (each 2.5 mM); 2 µL of cDNA; 1 µL of 10 µM forward primer; 1 µL of 10 µM reverse primer; and 12.3 µL of Milli-Q (registered trademark). As the primers for the amplification of the imine reductase gene, AtP2CR, the sequence of SEQ ID NO: 13 was used as the forward primer, and the sequence of SEQ ID NO: 14 was used as the reverse primer. For the amplification of the gene, MaP2CR, the sequence of SEQ ID NO: 15 was used as the forward primer, and the sequence of SEQ ID NO: 16 was used as the reverse primer. For the amplification of the gene, LjP2CR, the sequence of SEQ ID NO: 17 was used as the forward primer, and the sequence of SEQ ID NO: 18 was used as the reverse primer. The reaction was carried out by: repeating 30 cycles, each cycle consisting of an initial denaturation at 95° C. for two minutes, a subsequent denaturation at 95° C. for 30 seconds, an annealing at 60° C. for 30 seconds, and an elongation reaction at 72° C. for 1 minute and 10 seconds; and finally performing an elongation reaction at 72° C. for five minutes. The resulting reaction product was subjected to an electrophoresis using a 2% (w/v) agarose gel, which had been prepared with 1×TAE buffer (tris-acetic acid-EDTA buffer solution) stained with a DMSO solution of GelRed (trademark) nucleic acid gel stain (×10,000). After the electrophoresis, a single target band in the vicinity of 1100 bp was cut out with a scalpel from the surface of the agarose gel, and the cDNA was extracted using Wizard (registered trademark) SV Gel and PCR Clean-UP System (manufactured by Promega Corporation). The operation was carried out in accordance with the protocol accompanying the system.

Four µL of each resulting DNA fragment which had been purified, 1 µL of T-Vector pMD19 (manufactured by Takara Bio Inc.), and 5 µL of DNA ligation Kit Mighty Mix (manufactured by Takara Bio Inc.) were mixed, and a ligation reaction was carried out at a reaction temperature of 16° C. for 30 minutes. The resulting ligation solution was used to transform Escherichia coli DH5a.

In order to obtain the nucleotide sequence of each inserted DNA fragment, a sequencing reaction by BigDye (registered trademark) Terminator v3.1/1 Cycle Sequencing Kit (manufactured by Applied Biosystems) was carried out, using about 100 ng of the resulting plasmid. Each gene sequence was analyzed by subjecting the resulting sample to ABI PRISM (trademark) genetic analyzer.

The analysis of the inserted gene sequence has confirmed that the gene sequence of AtP2CR is the sequence of SEQ ID NO: 1, and the encoded amino acid sequence is the sequence of SEQ ID NO: 2. Further, it has been confirmed that the gene sequence of MaP2CR is the sequence of SEQ ID NO: 3, and the encoded amino acid sequence is the sequence of SEQ ID NO: 4, and that the gene sequence of LjP2CR is the sequence of SEQ ID NO: 5, and the encoded amino acid sequence is the sequence of SEQ ID NO: 6.

(2) Preparation of Expression Vectors

Each of the candidate genes AtP2CR, MaP2CR and LjP2CR which had been subcloned into the pMD19 vector in the section (1) above, was digested with the restriction enzymes and cleaved from the multicloning site. After confirming the digestion by electrophoresis, the target DNA fragment was cut out and purified. Thereafter, in the same manner as in the section (1) above, the purified DNA fragment of the clone was ligated into pGEX 4T-1 vector (manufactured by Takara Bio Inc.), which is a vector for expression in Escherichia coli that had likewise been subjected to restriction enzyme digestion, and transformation was carried out. About 18 hours later, the colony formed was grown in 2 mL of an LB liquid medium (100 µg/mL ampicillin), the plasmid extraction and the restriction enzyme digestion were carried out in the same manner as in the section (1) above, and the insertion of the sequence was confirmed. The thus constructed expression vectors were respectively named as pGEX-AtP2CR, pGEX-MaP2CR and pGEX-LjP2CR. The enzymes expressed by the respective vectors were all GST-fused proteins. It has been confirmed that the gene sequence of the GST-fused AtP2CR was the sequence of SEQ ID NO: 7, and the encoded amino acid sequence was the sequence of SEQ ID NO: 8, that the gene sequence of the GST-fused MaP2CR was the sequence of SEQ ID NO: 9, and the encoded amino acid sequence was the sequence of SEQ ID NO: 10, and that the gene sequence of the GST-fused LjP2CR was the sequence of SEQ ID NO: 11, and the encoded amino acid sequence was the sequence of SEQ ID NO: 12.

(3) Culture of Recombinant Bacteria

Each of the expression vectors prepared in the section (2) above was used to transform Escherichia coli BL21 (DE3). About 18 hours later, the colony formed was picked with a toothpick, transferred into 2 mL of an LB liquid medium (100 µL/mL ampicillin), and cultured overnight to prepare a pre-culture liquid. A quantity of 500 µL of the pre-culture liquid was added to 50 mL of an LB liquid medium (100 µg/mL ampicillin), followed by culturing at a culture temperature of 37° C. and at 225 rpm, until a turbidity (OD 600) of around 0.5 was reached. Thereafter, IPTG was added to a final concentration of 0.1 mM. The resultant was cultured at a culture temperature of 18° C. and at 150 rpm for about 18 hours. Further, the same expression operation was carried out, using, as a negative control, a vector into which no foreign gene had been inserted.

(4) Confirmation of Gene Expression

Each of the soluble protein fractions obtained in the section (3) above was purified (GST-tag purification) using GST-Tagged Protein Purification Kit (manufactured by Clontech Laboratories, Inc.) to obtain an enzyme solution. The operation was carried out in accordance with the protocol accompanying the kit.

Each enzyme solution (soluble protein) obtained by the GST-tag purification was subjected to SDS-PAGE, to confirm the expression of the target protein. As a result, it has been confirmed that each recombinant enzyme has a molecular weight of about 60 kDa, including that of the added tags of about 25 kDa.

<Example 2> (Confirmation of Activities of Plant-Derived Imine Reductases)

(1) Enzyme Reaction

An enzyme reaction was carried out using each enzyme solution (purified P2CR recombinant enzyme solution) obtained in Example 1. The reaction was carried out using a 1.5 mL Eppendorf tube as the reaction vessel, and using each enzyme reaction solution in a volume of 100 µL. Since PipC2 which serves as the substrate is not commercially available, one obtained from L-lysine by enzyme synthesis, using the aminotransferase MaALD1 obtained in Reference Example 1 to be described later, was used. The composition of the PipC2 enzyme reaction solution is shown in Table 2.

TABLE 2

|  | Final concentration | Volume of liquid added (µL) |
|---|---|---|
| 1M Tris-HCl buffer (pH 7.2) | 100 mM | 10 |
| 100 mM 2-oxoglutarate | 15 mM | 15 |
| 100 mM L-lysine | 10 mM | 10 |
| 5 mM Pyridoxal-5-phosphate | 0.1 mM | 2 |
| Pure water | — | 43 |
| Solution of enzyme MaALD1 | — | 20 |
| Total volume |  | 100 |

The enzyme reaction was carried out using a shaking incubator (manufactured by AS ONE Corporation), at a reaction temperature of 30° C. with shaking at 1,000 rpm. The reaction time was set to 120 minutes. Heating was performed at a reaction temperature of 98° C. for five minutes to inactivate the enzyme, and the reaction was terminated. Subsequently, the reaction solution was centrifuged at 15,000 rpm at room temperature for 10 minutes, and the resulting supernatant was used as a PipC2 enzyme synthesis solution.

To the thus obtained PipC2 enzyme synthesis solution, *NADPH was added to a final concentration of 10 mM, and 20 µL of each purified P2CR recombinant enzyme obtained in Example 1 was further added. Thereafter, the reaction was carried out under the same conditions as the reaction using the enzyme MaALD1 described above, to obtain an enzyme reaction product.

(2) Analysis of Enzyme Reaction Products

Each of the enzyme reaction products was analyzed by liquid chromatography-mass spectrometry (LCMS). First, each sample (enzyme reaction product) was subjected to a derivatization treatment. Using AccQ·Tag Ultra Derivatization Kit (manufactured by Waters Corporation), a mixture of each sample was prepared according to the composition shown in Table 3. The derivatizating reagent solution was added at last. After mixing, the mixture was incubated at 55° C. for 10 minutes.

TABLE 3

|  | Volume of liquid added (µL) |
|---|---|
| AccQ Tag Ultra Borate buffer | 60 |
| Pure water | 18 |
| Sample (enzyme reaction product) | 2 |
| Derivatizing reagent solution | 20 |
| Total volume | 100 |

Each sample which had been subjected to the derivatization treatment was diluted two-fold with pure water, and used as a sample for LCMS analysis. The conditions for HPLC-MS analysis are shown in Table 4.

TABLE 4

| Apparatus | UPLC-EST-MS/MS |
|---|---|
| Column | ACQUITY(manufactured by Waters Corporation) AccQ Tag Ultra Column (2.1 × 100 mm, 1.7 µm)(manufactured by Waters Corporation) |
| Column oven | 30° C. |
| Flow velocity | 0.2 ml/h |
| Solvent | Two-component mixture Solvent A: 10% AccQ Tag solution A Solvent B: 100% AccQ Tag solution B |
| Elution conditions | 0-15 min: 100% A, 0% B 15-25 min: 40% A, 60% B 25-27 min: 100% A, 0% B |
| Injection volume | 5 µL |
| Measurement mode | Positive ion mode |
| Cone voltage (V) | 60 |
| Collision voltage (V) | 50 |

When the activities of the enzyme reaction products were analyzed by LCMS analysis, it was confirmed that the products had the same retention time as that of L-PipA as the standard, and that novel peaks of the MS pattern were observed. Further, it was unable to detect PipA in the control.

The results have revealed that AtP2CR, MaP2CR and LjP2CR have the ability to reduce PipC2 to convert to PipA.

The enzyme reaction products were subjected to an HPLC analysis, using a chiral column, Astec CLC-D 4.6×150 mm (5 m) (manufactured by Sigma-Aldrich Co. LLC.), in order to determine whether each produced PipA is L-PipA or D-PipA. The results are shown in FIG. 1. The results have revealed that all of the P2CR enzyme reaction products obtained from three types of plants, *Arabidopsis thaliana*, *Lathyrus japonicus* and *Morus alba* are L-pipecolic acids.

(3) Analysis of Enzymatic Catalytic Activity

The PipC2 enzyme reaction solution was prepared in the same composition as the section (1) in Example 2. To the PipC2 enzyme reaction solution, *NADPH was added such that the final concentration in the total volume of 1 mL after the addition of each enzyme solution was 500 µM, 300 µM, 150 µM, 80 µM, 40 µM, 20 µM or 10 µM. Finally, 50 mM Tris-HCl (pH 7.2) was added to each resulting enzyme reaction solution to a total volume of 900 µL. These solutions were used as the reaction solutions.

To each of these reaction solutions, 100 μL of the purified AtP2CR recombinant enzyme solution obtained in Example 1 was added, and the reaction was initiated. The absorbance at 340 nm was measured from the start of the reaction, and measurement was carried out for 10 minutes. The same experiment was repeated three times, and the mean value was calculated.

The reaction velocity was calculated from the resulting measured value. Using the calculated reaction velocity, the respective kinetic parameters (Michaelis constant Km and maximum reaction velocity Vmax) were calculated, in accordance with the Hanes-Woolf plot (Hanes C S., (1932), vol. 26, 5, 1406, Biochemical Journal).

The reaction, measurement and calculation were carried out also for LjP2CR in the same manner as for AtP2CR.

For MaP2CR, the reaction, measurement and calculation were carried out in the same manner as for AtP2CR, except that the reaction was carried out under the conditions where the above-described *NADPH concentration was 80 μM, 40 μM, 20 μM, 10 μM, 2 μM, 1 μM or 0.5 μM.

The change in the measured absorbance was converted to the change in the concentration of *NADPH, using the molar absorption coefficient of *NADPH, 6.3×10 (1/mmol·cm). From the resulting value, the reaction velocity (μM/s) in the decrease in *NADPH was calculated. It is noted that the value of the period during which the absorbance showed a linear decrease from the start of the measurement, was used as the decreased value of the absorbance.

Figure 2:
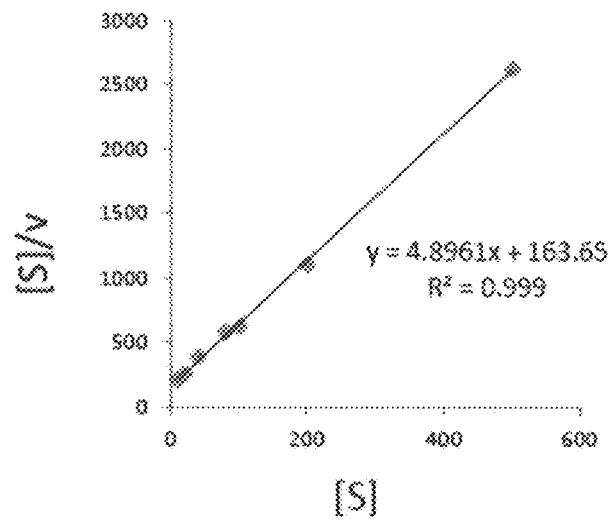
FIG. 2 shows the linear approximation of the Hanes-Woolf plot, obtained in the section of (3) Analysis of Enzymatic Catalytic Activity in Example 2.
Figure 2:
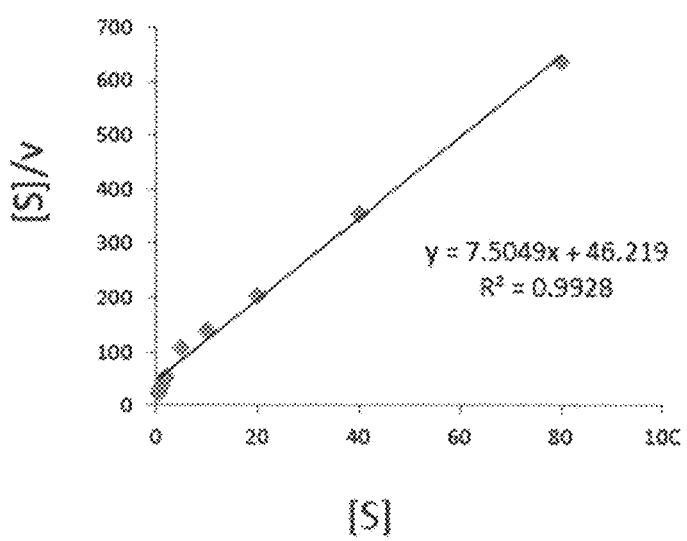
Figure 2:
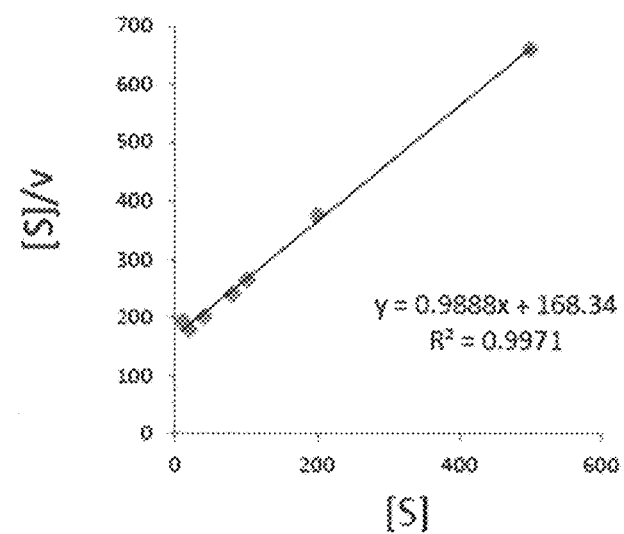

The values of the substrate concentration/the reaction velocity in the respective *NADPH concentrations were plotted, to obtain the linear approximation of the Hanes-Woolf plot. The results are shown in FIG. 2. In FIG. 2, (1) shows the result of AtP2CR, (2) shows the result of MaP2CR, and (3) shows the result of LjP2CR. Since R2 was 0.99 in all of the results of the three P2CRs, it is considered that highly reliable results have been obtained. In each of the graphs of the Hanes-Woolf plot, the inclination is 1/Vmax, and the intersection with the x axis is Km. The maximum reaction velocity Vmax and the Km were calculated by the Hanes-Woolf equation. AtP2CR had a Vmax of 208.73 nmol/min/mg and a Km of 33.42 μM, MaP2CR had a Vmax of 24.00 nmol/min/mg and a Km of 6.16 μM, and LjP2CR had a Vmax of 199.55 nmol/min/mg and a Km of 170.24 μM.

Figure 3:
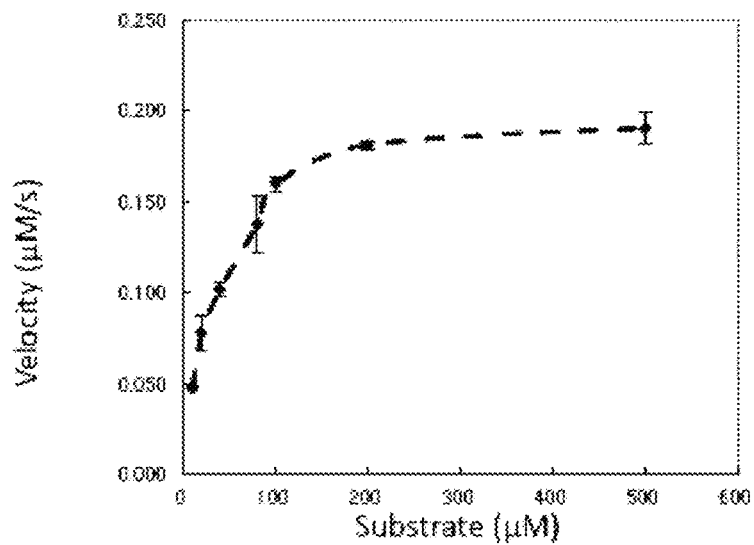
FIG. 3 shows the Michaelis-Menten model by ANEMONA, obtained in the section of (3) Analysis of Enzymatic Catalytic Activity in Example 2.
Figure 3:
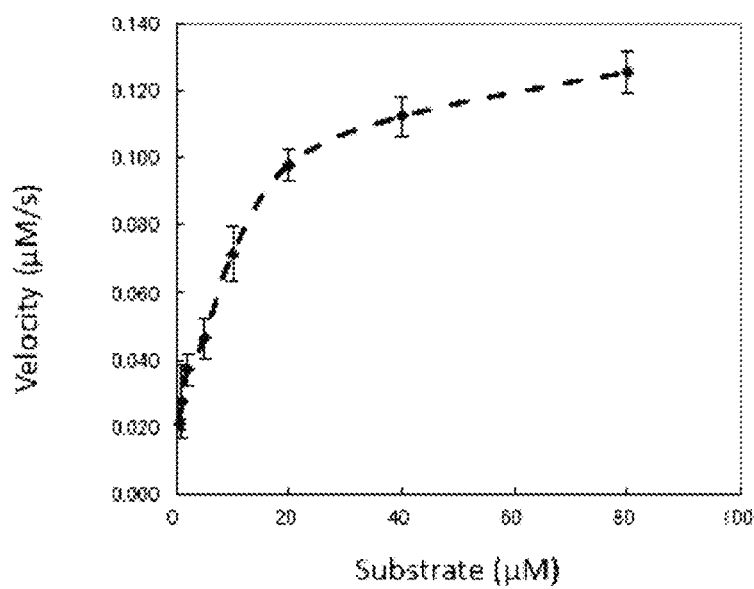
Figure 3:
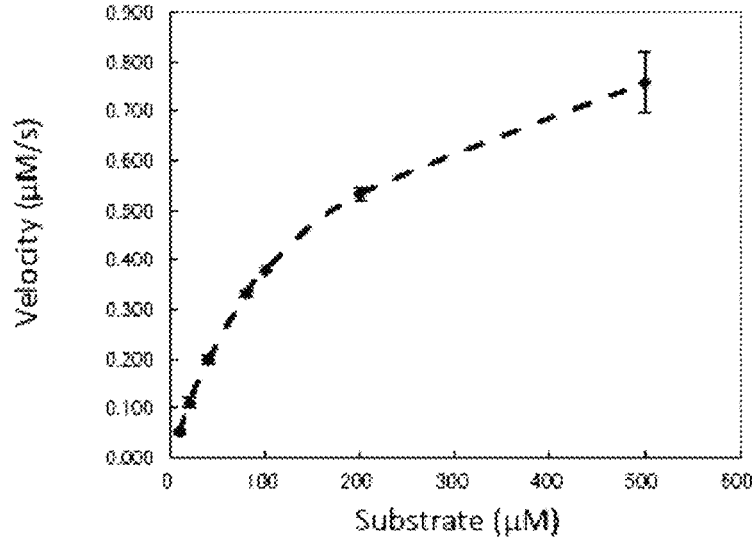

Further, a nonlinear regression analysis was carried out by ANEMONA (Hernandez and Ruiz, (1998) 14, 2, 227, Bioinformatics), and the Vmax and Km were calculated in the same manner as described above. The graphs illustrating the Michaelis-Menten model by ANEMONA are shown in FIG. 3. In FIG. 3, (1) shows the result of AtP2CR, (2) shows the result of MaP2CR, and (3) shows the result of LjP2CR. AtP2CR had a Vmax of 215.5 nmol/min/mg and a Km of 34.29 μM, MaP2CR had a Vmax of 21.2 nmol/min/mg and a Km of 3.57 μM, and LjP2CR had a Vmax of 187.3 nmol/min/mg and a Km of 155.03 μM.

While the two methods, the Hanes-Woolf plot and ANEMONA, yielded similar Vmax and Km values, the values determined by nonlinear regression were thought to be closer to the true values of Vmax and Km. Therefore, the values determined by ANEMONA were used as the Vmax and Km.

TABLE 5

| | Literature value dpkA (Enzyme derived from Microorganism) | Measured value | | |
|---|---|---|---|---|
| | | AtP2CR Arabidopsis Thaliana | MaP2CR Morus alba | LjP2CR Lathyrus japonicus |
| NADP Vmax | 220 | 216 | 21 | 187 |
| NADP Km (uM) | 140.0 | 34.3 | 3.6 | 155.0 |
| Molecular weight of enzyme | 35954 | 61870 | 61792 | 63449 |
| Activity per one molecule of enzyme kcat (1/min) | 7.9 | 13.3 | 1.3 | 11.9 |
| Vmax/Km | 1.6 | 6.3 | 6.9 | 1.2 |
| Catalytic activity (kcat/km) | 56 | 389 | 367 | 77 |

(km:mM)
*AtP2CR, MaP2CR and LjP2CR are all GST-fused proteins.

It is disclosed in the literature (Muramatsu et al., (2005), vol. 280, 7, 5329 THE JOURNAL OF BIOLOGICAL CHEMISTRY) that the PipC2 reductase dpkA derived from the microorganism *Pseudomonas putida*, which is used as an enzymatic catalyst for industrial production of PipA, has a Vmax of 220 nmol/min/mg and a Km pf 140 μM.

As shown in Table 5, the value of the index, Kcat/km, of the catalytic activity calculated from the literature is 56, but the Kcat/km values of the enzymes of the present invention were all above 56. Accordingly, it has been found out that all of AtP2CR, MaP2CR and LjP2CR have an excellent ability to reduce PipC2 to convert to PipA, and are excellent enzymatic catalysts that are enzymatically stable.

<Reference Example 1> (Preparation of Plant-Derived Lysine Aminotransferase MaALD1)

(a) Cloning of Plant-Derived Lysine Aminotransferase Gene MaALD1

RNA extraction was performed, from the leaves of *Morus alba* which had been grown for about one month after germination, using RNeasy Plant Mini Kit (manufactured by QIAGEN, Inc.). From the resulting total RNA, the cDNA was synthesized, using ReverTra Ace (registered trademark) qPCR RT Master Mix with gDNA Remover (manufactured by TOYOBO Co., Ltd.).

The resulting cDNA was used as a template to carry out a PCR reaction. The primers MaALD1-FW (GGATC-CATGACGCATAATTATTCTCAG) (SEQ ID NO: 20) and MaALD1-RV (GTCGACTCATTTGTAAAGAGATTT-TAGTC) (SEQ ID NO: 21) were used for the PCR reaction. The reaction was carried out based on the protocol of TaKaRa Ex Taq (registered trademark) Hot Start Version (manufactured by Takara Bio Inc.).

The purified DNA was cloned into T-Vector pMD19 (manufactured by Takara Bio Inc.). The result of the sequence analysis confirmed that this was the gene encoding the aminotransferase MaALD1 (SEQ ID NO: 19). The gene region of MaALD1 which had been subcloned into the pMD19 vector was digested with restriction enzymes BamHI and SalI, and cleaved from the multicloning site. After confirming the digestion by electrophoresis, the target DNA fragment was cut out and purified. Thereafter, the purified DNA fragment was ligated into pCold ProS2 vector (manufactured by Takara Bio Inc.), which is a vector for expression in *Escherichia coli* that had likewise been subjected to restriction enzyme digestion. The resulting solution was used to transform *Escherichia coli* DH5a, to construct the target plasmid. The resulting plasmid was named pCold-MaALD1.

(b) Expression of Recombinant Enzyme

*Escherichia. Coli* (BL21 strain) was transformed, using the expression vector pCold-MaALD1 prepared in the section (a) above. About 18 hours later, the colony formed was picked with a toothpick, transferred into 2 mL of an LB liquid medium (100 μL/mL ampicillin), and cultured overnight to prepare a pre-culture liquid. A quantity of 500 μL of the pre-culture liquid was added to 50 mL of an LB liquid medium (100 μg/mL ampicillin), followed by culturing at a culture temperature of 37° C. and at 225 rpm, until a turbidity (OD 600) of around 0.5 was reached. Thereafter, the pCold-MaALD1 transformant was left to stand on ice for 30 minutes, and IPTG was added to a final concentration of 0.1 mM. The resultant was cultured at a culture temperature of 15° C. and at 150 rpm for about 18 hours.

(c) Purification of Recombinant Enzyme

The culture liquid obtained in the section (b) above was transferred to a 50 mL Falcon (registered trademark) tube and centrifuged at 2,330×g and at 4° C. for 10 minutes.

The supernatant was discarded, and 5 mL of 1×PBS (phosphate-buffered saline) was added to the cells. The resulting mixture was resuspended by vortexing, and then centrifuged under the same condition as the previous centrifugation to wash the cells. The above-described operation was repeated twice.

To the collected cells, 4 mL of a sonication buffer {50 mM Tris-HCl (pH: 7.5), 150 mM NaCl, 10% (v/v) Glycerol, 5 mM dithiothreitol (DTT)} was added, and the cells were disrupted by sonication (50% duty, output 2, 30 seconds× twice). The disrupted cells were centrifuged at 15,000 rpm and at 4° C. for 10 minutes, and the supernatant was obtained as the soluble protein fraction, and the sediment was obtained as the insoluble protein fraction.

The thus obtained soluble protein fraction was purified using His-Tagged Purification Miniprep Kit (manufactured by Clontech Laboratories, Inc.), to obtain MaALD1.

The invention claimed is:

1. A method of producing an L-cyclic amino acid, the method comprising bringing a cyclic amino acid having a double bond at the 1-position and having the following general formula (I):

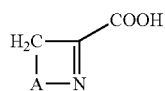

wherein A is an alkylene chain which has a chain length of from 1 to 4 atoms, which contains or does not contain at least one hetero atom selected from the group consisting of a sulfur atom, an oxygen atom and a nitrogen atom, in the chain or at the end of the chain, and which has or does not have a substituent, into contact with a polypeptide shown in (A), (B) or (C) below, a microorganism or cell having the ability to produce said polypeptide or comprising said polypeptide, a processed product of the microorganism or the cell, and/or a culture liquid obtained by culturing the microorganism or the cell and comprising said polypeptide, to produce an L-cyclic amino acid having the following general formula (II):

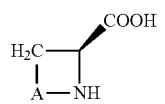

wherein A is the same as defined above:
(A) a polypeptide comprising the amino acid sequence of SEQ ID NO: 2, 4, 6, 8, 10 or 12;
(B) a polypeptide which comprises the amino acid sequence of SEQ ID NO: 2, 4, 6, 8, 10 or 12 except that 1 to 10 amino acids are deleted, conservatively substituted and/or added, and which has the ability to catalyze the reaction of the following formula (1) to produce the L-cyclic amino acid:

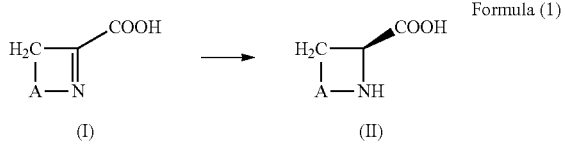

wherein A is the same as defined above;
or
(C) a polypeptide which comprises an amino acid sequence having a sequence identity of 95% or more to the amino acid sequence of SEQ ID NO: 2, 4, 6, 8, 10 or 12, and which has the ability to catalyze the reaction of the formula (1) to produce the L-cyclic amino acid.

2. The method of producing an L-cyclic amino acid according to claim 1, wherein the polypeptide is encoded by a nucleic acid shown in (D) or (E) below:
(D) a nucleic acid comprising the nucleotide sequence of SEQ ID NO: 1, 3, 5, 7, 9 or 11; or
(E) a nucleic acid which comprises the nucleotide sequence of SEQ ID NO: 1, 3, 5, 7, 9 or 11 except that 1 to 30 nucleotides are substituted, deleted and/or added, and which encodes a polypeptide having the ability to catalyze the reaction of the formula (1) to produce the L-cyclic amino acid.

3. A method of producing an L-cyclic amino acid, the method comprising:
allowing an acyclic α,ω-diamino acid having the following general formula (III):

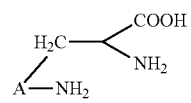

wherein A is an alkylene chain which has a chain length of from 1 to 4 atoms, which contains or does not contain at least one hetero atom selected from the group consisting of a sulfur atom, an oxygen atom and a nitrogen atom, in the chain or at the end of the chain, and which has or does not have a substituent, to react with an enzyme capable of converting the amino group at the α-position of the diamino acid to a keto group and producing an α-keto acid, to produce a cyclic amino acid having a double bond at the 1-position and having the following general formula (I):

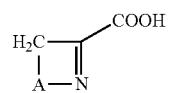

wherein A is the same as defined above;
and
then producing an L-cyclic amino acid having represented by the following general formula (II):

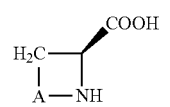

wherein A is the same as defined above, from the resulting cyclic amino acid having a double bond at the 1-position by the method according to claim 1.

4. The method of producing an L-cyclic amino acid according to claim 3, wherein the enzyme capable of converting the amino group at the α-position of the diamino acid to a keto group and producing an α-keto acid is one or more enzymes selected from the group consisting of a D-amino acid oxidase, an L-amino acid oxidase, a D-amino acid dehydrogenase, an L-amino acid dehydrogenase, a D-amino acid aminotransferase and an L-amino acid aminotransferase.

5. The method of producing an L-cyclic amino acid according to claim 1, wherein the cyclic amino acid having a double bond at the 1-position and having the general formula (I) is $\Delta^1$-piperidine-2-carboxylic acid, and the L-cyclic amino acid having the general formula (II) is L-pipecolic acid.

6. The method of producing an L-cyclic amino acid according to claim 1, wherein the substituent is selected from the group consisting of alkyl groups having from 1 to 4 carbon atoms, aryl groups having from 6 to 12 carbon atoms, alkoxy groups having from 1 to 4 carbon atoms, carboxyl group, halogen groups, cyano group, amino group, nitro group and hydroxyl group.

7. The method of producing an L-cyclic amino acid according to claim 3, wherein the substituent is selected from the group consisting of alkyl groups having from 1 to 4 carbon atoms, aryl groups having from 6 to 12 carbon atoms, alkoxy groups having from 1 to 4 carbon atoms, carboxyl group, halogen groups, cyano group, amino group, nitro group and hydroxyl group.

\* \* \* \* \*